(12) United States Patent
Kirihara et al.

(10) Patent No.: US 9,228,968 B2
(45) Date of Patent: Jan. 5, 2016

(54) THERMAL SENSOR AND PLATFORM

(75) Inventors: Akihiro Kirihara, Tokyo (JP); Shinichi Yorozu, Tokyo (JP)

(73) Assignee: NEC CORPORATION, Tokyo (JP)

( * ) Notice: Subject to any disclaimer, the term of this patent is extended or adjusted under 35 U.S.C. 154(b) by 610 days.

(21) Appl. No.: 13/636,950

(22) PCT Filed: Mar. 8, 2011

(86) PCT No.: PCT/JP2011/055300
§ 371 (c)(1),
(2), (4) Date: Nov. 5, 2012

(87) PCT Pub. No.: WO2011/118374
PCT Pub. Date: Sep. 29, 2011

(65) Prior Publication Data
US 2013/0044787 A1    Feb. 21, 2013

(30) Foreign Application Priority Data

Mar. 25, 2010  (JP) ................................. 2010-070610

(51) Int. Cl.
| | |
|---|---|
| *G01K 7/00* | (2006.01) |
| *G01N 27/16* | (2006.01) |
| *G01J 5/02* | (2006.01) |
| *G01J 5/10* | (2006.01) |
| *H01L 27/22* | (2006.01) |
| *H01L 37/00* | (2006.01) |
| *G01N 33/00* | (2006.01) |
| *H01L 43/00* | (2006.01) |

(52) U.S. Cl.
CPC ................ *G01N 27/16* (2013.01); *G01J 5/025* (2013.01); *G01J 5/10* (2013.01); *H01L 27/22* (2013.01); *H01L 37/00* (2013.01); *G01N 33/0075* (2013.01); *H01L 43/00* (2013.01)

(58) Field of Classification Search
None
See application file for complete search history.

(56) References Cited

U.S. PATENT DOCUMENTS

| | | | |
|---|---|---|---|
| 8,164,148 B2* | 4/2012 | Kim et al. | 257/421 |
| 2007/0209437 A1* | 9/2007 | Xue et al. | 73/514.31 |
| 2007/0253121 A1 | 11/2007 | Yamada et al. | |
| 2009/0201614 A1 | 8/2009 | Kudo et al. | |
| 2010/0149862 A1* | 6/2010 | Ishiwata et al. | 365/171 |

(Continued)

FOREIGN PATENT DOCUMENTS

| | | |
|---|---|---|
| JP | 8-128982 A | 5/1996 |
| JP | 2006-032570 A | 2/2006 |
| JP | 2006-300623 A | 11/2006 |

(Continued)

OTHER PUBLICATIONS

International Preliminary Report on Patentability issued Oct. 2, 2012 in PCT/JP2011/055300.

(Continued)

*Primary Examiner* — Lisa Caputo
*Assistant Examiner* — Nasir U Ahmed
(74) *Attorney, Agent, or Firm* — Sughrue Mion, PLLC

(57) ABSTRACT

In order to provide a sensor operating in a high sensitivity at a low cost and a radio sensor platform having a high energy efficiency, the sensor includes a detecting film which generates heat through incidence or adhesion of an object, a magnetic film which generates a spin current in a direction of a temperature gradient by the heat generated by the detecting film, and an electrode which convert the spin current generated by the magnetic film into an electric current.

3 Claims, 34 Drawing Sheets

(56) References Cited

U.S. PATENT DOCUMENTS

2010/0225312 A1* 9/2010 Nakamura et al. ............ 324/300
2010/0276770 A1* 11/2010 Uchida et al. ................. 257/421

FOREIGN PATENT DOCUMENTS

| | | |
|---|---|---|
| JP | 2007-122550 A | 5/2007 |
| JP | 2007-294710 A | 11/2007 |
| JP | 2009-130070 A | 6/2009 |
| JP | 2009-194070 A | 8/2009 |
| JP | 2009-295824 A | 12/2009 |
| JP | 2010-205975 A | 9/2010 |
| WO | 2009/151000 A1 | 12/2009 |

OTHER PUBLICATIONS

Daniel D. Stancil, et al., "Spin Waves: Theory and Applications", Springer-Verlag, 2009, pp. 139-168.
Alexander Khitun, et al., "Spin Wave Magnetic NanoFabric: A New Approach to Spin-Based Logic Circuitry", IEEE Transactions on Magnetics, Sep. 2008, pp. 2141-2152, vol. 44, No. 9.
Shuichi Murakami, et al., "Dissipationless Quantum Spin Current at Room Temperature", Science, Sep. 2003, pp. 1348-1351, vol. 301, No. 5638.
E. Saitoh, et al., "Conversion of spin current into charge current at room temperature: Inverse spin-Hall effect", Applied Physics Letters, 2006, pp. 182509-1-182509-3, vol. 88, Issue 18.
International Search Report of PCT/JP2011/055300 dated Jun. 14, 2011.
Communication dated Dec. 5, 2014, issued by the Japanese Patent Office in counterpart Japanese application No. 2012-506914.
K. Ando et al., Observation of inverse spin-hall effect using spin pumping, Solid State Physics, AGNE Gijutsu Center Inc., Aug. 15, 2007, vol. 42, No. 8, pp. 19-27.
K. Uchida et al., Observation of the spin Seebeck effect, Nature, Macmillan Publishers Limited, Oct. 9, 2008, vol. 455, pp. 778-781.

* cited by examiner

TAKE CONTENTS OF MAGNETIC MEMORY IN PHASE DATA OF SPIN WAVE
SPIN CURRENT

THERMAL SENSOR AND PLATFORM

CROSS REFERENCE TO RELATED APPLICATIONS

This application is a National Stage of International Application No. PCT/JP2011/055300 filed Mar. 8, 2011, claiming priority based on Japanese Patent Application No. 2010-070610 filed Mar. 25, 2010, the contents of all of which are incorporated herein by reference in their entirety.

TECHNICAL FIELD

The present invention is related to a thermal sensor utilizing the spintronics technique which uses the charges and spins of electrons in a solid, and a platform which drives the same.

BACKGROUND ART

The importance of the sensor network technique is increasing which has a radio communication function as an interface between a real space and a virtual space in a computer graphics in the ubiquitous society. In the sensor network, many radio sensor nodes carry out sensing operations to transmit the obtained data, respectively. The transmitted data are collected by a server. Thus, various situations in a wide range such as traffic jam and environments can be grasped.

As the sensor node (sensor terminal), there is the node which is provided with a sensor section which detects physical data, a signal processing section which executes analog-to-digital conversion, calculation processing of the physical data, a radio section which transmits the processed data, and a power supply section which supplies power to each of these sections (for example, refer to Patent Literature 1).

As the sensor section, various types of sections are used according to the application. For example, an infrared sensor is extensively used in an information security field and a remote sensing field. The infrared sensors can be divided into a quantum type infrared sensor and a thermal type infrared sensor. The quantum type infrared sensor has a high efficiency in the sensitivity and the speed of response and so on, but generally needs the cooling and a high cost. Therefore, the quantum type infrared sensor is not too much used for a consumer use.

On the other hand, the thermal type infrared sensor does not need the cooling and is a comparatively low cost, because the sensor detects heat generation through absorption of infrared rays. As the thermal type infrared sensor, a pyroelectric type infrared sensor which detects heat generation due to the infrared rays by using the pyroelectric effect of ferroelectric substance, a bolometric type infrared sensor which detects heat generation due to the resistance change, and a thermopile type infrared sensor which detects thermoelectromotive force by using the thermoelectric effect and so on are exemplified.

A power supply section is often composed of primary battery. However, recently, a method of using radio power supply and a method of collecting power through the environment generation are used. As a method of the environment generation, photoelectric conversion using solar photovoltaic power generation, and vibration conversion which converts vibration into electricity by a piezoelectric element, thermoelectric conversion which converts heat into electrical energy and so on are used.

In the signal processing section, the analog-digital conversion of the obtained raw data, the integration, organization and conversion of the obtained data, and a control for radio communication and so on are mainly carried out. The signal processing section codes data for the radio communication according to the necessity. The signal processing section does not need a large-scale and high-speed processing unlike the personal computer. In the present situation, as the signal processing section, a comparatively small-scale microcomputer is used. The processing ability of the microcomputer is about 8 bits and the clock frequency is several MHz to tens of MHz. In this case, because the long life operation is important, a small power consumption amount than the conventional processor is strongly required. Also, although being different from the other information processing system, in the sensor, a standby time during which measurement and communication are carried out becomes long. Therefore, a sleep mode is also important in which a low power operation or an operation stop is carried out while an internal state is maintained.

The radio section communicates through use of a microwave oscillator and a receiver. However, high capacity communication and high power oscillation are not always needed unlike a mobile phone and a wireless LAN. As the radio communication method, Zigbee (frequency: the 2.4 GHz band, transmission rate: 250 kbps, maximum communication distance: 30 m) and so on are often used which is for a short distance communication and has a comparatively low power consumption amount. However, recently, further power saving method is proposed and studied.

Also, as a new technique which can contribute to the above ubiquitous sensor network, spintronics is remarkable in recent years. The spintronics is a technique that the degree of freedom of the spin is newly utilized effectively in addition to the degree of freedom of the electric charge, and is expected in a low power consumption amount of information processing and application to a new energy conversion. For example, an electric current is necessarily accompanied by the joule heat generation. On the other hand, the spin current which is a flow of spins, can realize information communication in a very small energy loss from the physical property (for example, refer to Patent Literature 2). Also, the spin current can be flow even in insulator in which electrons are restrained, and completely new utilization is expected for the information processing and the sensing (for example, Non-Patent Literature 1, and Non-Patent Literature 2).

Some techniques which convert the spin current into another physical quantity are known. For example, a technique which uses a spin Hall effect is known as the technique which converts an electric current into the spin current. The spin Hall effect has the effect that when applying an electric current into material, the spin current is generated in a direction orthogonal to a direction of the electric current (for example, refer to Non-Patent Literature 3). Oppositely, a reverse spin Hall effect is found in which the electric current is generated in a direction perpendicular to a direction of the spin current (for example, refer to Non-Patent Literature 4).

Also, as a technique which generates the spin current from a spatial temperature gradient, a spin Seebeck effect has been reported. The spin current generated by the heat can be taken out as the electric current through the reverse spin Hall effect (for example, refer to Patent Literature 3).

CITATION LIST

Patent Literature

[Patent Literature 1] JP 2007-122550A
[Patent Literature 2] JP 2009-295824A

[Patent Literature 3] JP 2009-130070A

Non-Patent Literature

[Non-Patent Literature 1]
Daniel D. Stancil, Anil Prabhakar, "Spin Waves: Theory and Applications" Springer-Verlag pp. 139-168 (2009)
[Non-Patent Literature 2]
Alexander Khitun, MingqiangBao, and Kang L. Wang, "Spin Wave Magnetic NanoFabric: A New Approach to Spin-Based Logic Circuitry" IEEE Transactions on Magnetics, Vol. 44, No. 9 p. 2141 (2008)
[Non-Patent Literature 3]
Shuichi Murakami, et al., "Dissipationless Quantum Spin Current in Room Temperature" Science, Vol. 301, p. 1348 (2003)
[Non-Patent Literature 4]
E. Saitoh, M. Ueda, and H. Miyajima, "Conversion of the spin current into charge current in room temperature: inverse spin-Hall effect" Applied Physics Letters, Vol. 88, p. 182509 (2006)

SUMMARY OF THE INVENTION

In the sensor terminal for the radio sensor network described so far, there are some problems in the present situation. For example, although the sensor terminal must have high energy efficiency (long life operation), high detection sensitivity, low cost, and high convenience, it is generally difficult to attain all of them at a time.

A specific problem will be described by using an infrared sensor as an example while depending on each sensor section. First, because requiring the cooling, it is difficult to apply the quantum-type infrared sensor to the consumer-use sensor network. As for the thermal type infrared sensor which the cooling is unnecessary to, some problems are given to each type. For example, the pyroelectric type infrared sensor has shortcomings in which monolithic integration is difficult, resulting in the high cost, and which is sensitive to vibration. Also, the bolometer type infrared sensor has shortcomings in which a read circuit is complicated to detect a resistance change, in addition to a cost problem such as formation of a bolometer film (vanadium oxide and so on). The thermopile type infrared sensor can be produced in the comparatively low cost, but because the thermoelectric conversion efficiency is low, enough sensitivity is not obtained in the present situation.

Also, in order to make thermal capacity of the detection section as small as possible even in any thermal type infrared sensor, a micromachining process is necessary for making a detecting section hollow to prevent heat conduction to the substrate. In addition, the wiring needs be formed to be as thin as possible, so as to suppress the heat conduction from the wiring to the minimum. In order to adiabatically separate detection section, it is desirable to use material with a small heat transfer rate for wirings and support sections. However, the material which can be used is constrained because electrically detecting heat, the material with a comparatively large heat transfer rate such as silicon nitride is used in present, resulting in the high cost and the low yield for the above fine fabrications.

Also, there is a big problem in the power supply section in addition to the sensor section. When sensor terminals are arranged in any places, the supply of power from outside to them is generally difficult. Therefore, a cell is often provided in the power supply section of each terminal. In this case, however, because of the power which is necessary for the signal processing and the radio communication, the super long life operation is difficult and the work to exchange the cell on the way occurs.

As a maintenance-free power supply, the techniques of the environment generation (energy harvesting) by using sun light, vibration, and thermoelectric conversion is expected. However, high efficient power generation in sun light is limited in case of the outside of a house and the fine weather (intermittency). There are many constrains as only in case where vibration is constantly given, in the vibration power generation.

The use of heat has a comparatively high convenience depending on the use scene such as use of the body temperature, the solar heat, and various types of waste heat of a car, electrical and electronic equipments and so on. However, the energy conversion efficiency of the conventional thermoelectric conversion device which is based on the Seebeck effect is nit high. The dimensionless performance index ZT of the thermoelectric conversion material is proportional to the electrical conductivity and is in inverse proportion to the heat transfer rate. However, they generally have a correlation (a material that is easy for electric current to flow is easy to pass away heat). Therefore, ZT=about 1 to 2 (bulk material) which is an upper limit in case of metal and semiconductor. For this reason, even if a watch with small power consumption amount can be operated, there is a problem in the stable power supply to a radio sensor terminal.

Also, in order to make a long life operation and the application of the environment generation technique possible, it is required to restrain the power consumption amount as a whole terminal. Therefore, it is desirable to further reduce the power consumption amount in the signal processing section and the radio section. Especially, in case of the sensor terminal, it is very important to reduce standby power in the sleep mode. However, in the conventional electronics device, because of the leak electric current and so on, it is difficult to bring standby power close to 0.

As mentioned above, a sensor operating in a high sensitively at a low cost and a radio sensor platform in high energy efficiency have not realized up to this.

A thermal sensor according to the present invention is provided with a detecting film configured to generate heat through incidence or adhesion of an object to be detected, a magnetic film configured to generate a spin current in a direction of a temperature gradient by the heat generated by the detecting film, and an electrode configured to convert the spin current generated by the magnetic film into an electric current.

In the above-mentioned thermal sensor, it is desirable that the detecting film is an infrared ray absorption film which generates the heat by absorbing at least a part of the infrared ray.

In the above-mentioned said thermal sensor, it is desirable that the detecting film is a gas absorption catalyst film which contains a catalyst which generates the heat through a chemical reaction by gas absorption.

In the above-mentioned said thermal sensor, it is desirable that the magnetic film is formed of a magnetic insulator.

A platform according to the present invention is provided with a sensor section configured to detect a predetermined condition; a spin current generating section configured to generate a spin current thermally from a spatial temperature gradient, and a signal processing section configured to incorporate sensing data according to the condition detected by the sensor section into the spin current generated by the spin current generating section and carry out signal processing.

It is desirable that the above platform is provided with a radio section configured to transmit in microwave, data which contains the sensing data subjected to a signal processing by the signal processing section.

In the above platform, it is desirable that the spin current generating section is provided with a spin Seebeck device having an end portion or a part of a waveguide arranged in neighborhood of a hot or cold heat source and configured to thermally generate a spin wave spin current in the waveguide.

It is desirable that the waveguide of the spin Seebeck device is formed of magnetic insulator.

It is desirable that the waveguide of the spin Seebeck device has a structure that a width of the waveguide is modulated periodically, a structure that has a periodic ditch on a surface of the waveguide, or a structure which has a periodic ferromagnetic film through a barrier layer on the surface of the waveguide.

In the platform, it is desirable that the signal processing section incorporates the sensing data into the spin current generated by the spin current generating section, and then carries out signal processing by using phase information or route information of the spin wave spin current generated by the spin current generating section as a state variable.

In the platform, it is desirable that the signal processing section is provided with any of a spin current combining device which connects a plurality of waveguides for input to one waveguide for output, a spin current branching device which branches one waveguide for input to a plurality of waveguides for output, a spin current partial reflection mirror which partially reflects the spin current transmitted through the waveguide, and a spin current modulator which carries out a phase shift of the spin current transmitted through the waveguide in response to the control signal.

In the platform, it is desirable that an inputted spin wave spin current is divided into two by the spin current partial reflection mirror of a 3-terminal type, one of the spin wave spin currents outputted from the spin current partial reflection mirror receives the phase shift based on the sensing data by the spin current modulator, and the signal processing section is provided with a spin current interference device which changes a propagation route of the spin current based on an interference result of the other of the spin wave spin currents outputted from the spin current partial reflection mirror and the spin wave spin current subjected to the phase shift by the spin current modulator by a spin current partial reflection mirror of a 4-terminal type.

In the platform, it is desirable that the spin current partial reflection mirror partially reflects the spin current by either of a gap, a domain wall, a magnetic field and a magnetic terminal.

In the platform, it is desirable that the spin current modulator carries out the phase shift of the spin current transmitted through the waveguide by modulating either of magnetic field, electric field, strain, a magnetic terminal and a domain wall in response to a control signal.

In the platform, it is desirable that the control signal is the sensing data or content stored in a magnetic memory.

It is desirable that the platform is provided with a spin Hall effect device which generates an electric current from the spin current generated by the spin current generating section and the control signal is an electric current generated by the spin Hall effect device.

In the platform, it is desirable that the signal processing section is provided with a majority gate which outputs a state variable from one waveguide according for output by combining the spin currents from three waveguides for input.

In the platform, it is desirable that the signal processing section has the spin current modulator on one of three waveguides for input to the majority gate, and a basic boolean algebra gate which has another spin current modulator on one of the waveguides for output from the majority gate.

In the platform, it is desirable that the signal processing section is provided with a basic calculation gate which uses the route data of a spin current interference spin current as a state variable, while combining a spin current interference device and the spin current modulator.

In the platform, it is desirable that the signal processing section is provided with a spin current processing circuit in which a plurality of basic calculation gates are combined.

In the platform, it is desirable that the radio section is provided with a spin current partial reflection mirror configured to partially reflect the spin current transmitted through the waveguide from the signal processing section, and a spin current resonator which generates a microwave by resonating the spin current inputted to the magnetism insulator from the spin current partial reflection mirror by arranging a metal terminal on the magnetism insulator and applying an electric current to the metal terminal.

According to the first viewpoint of the present invention, the thermal sensor can be configured which has a high sensitivity in a simple structure, by detecting a small amount of heat by using the degree of freedom of the spin current. When insulator material is used as the magnetic film, material with very small heat transfer rate can be adopted. Therefore, it becomes possible to generate the spin current efficiently in the state that a temperature gradient by the heat generation is maintained and it is possible to carry out the detection in high sensitivity. In addition, when detecting the heat generation by the spin current in the magnetism insulator, it is not necessary to directly attach electric wiring to the heat generation portion. The micromachining process for adiabatic structure can be omitted, and the high sensitive thermal type sensor can be configured in a comparatively simple structure, resulting in a low cost.

According to the second viewpoint of the present invention, the spin current can be generated from various heat sources such as the solar heat and the temperature, and various types of waste heat. By using a generated spin current as a base, the acquisition of sensing data, simple signal processing such as the integration, arrangement and encryption, and the microwave oscillation for radio communication are carried out. Also, because joule heat generation is not accompanied in the spin current through the magnetism insulator in the waveguide, it is possible carry out information transmission and information processing with small energy dissipation, so that the platform of high energy efficiency can be built. Also, by using the spin current in the spin current generating section which drives a sensor and the signal processing section, the platform with high energy efficiency can be built. Also, in the spin current modulator, a reconfigurable circuit which can store a procedure and so on in a non-volatile manner, can be built by using a magnetic material such as a magnetic terminal and a domain wall as a gate terminal. Therefore, the standby power can be reduced by use of a sleep mode and so on. Moreover, the spin current on which the sensing data has been reflected is converted into the microwave just as it is, and as the result, the radio communication of high energy efficiency becomes possible.

DESCRIPTION OF EXEMPLARY EMBODIMENT

A thermal sensor according to a first exemplary embodiment of the present invention includes a detecting film which generates heat with incidence or adhesion of an object to be detected, a magnetic film which generates a spin current in a direction of a temperature gradient due to the heat generated in the detecting film, and an electrode which converts the spin current generated by the magnetic film into an electric current.

A platform according to a second exemplary embodiment of the present invention includes a sensor section which detects a predetermined state, a spin current generating section which generates a spin current thermally from a spatial temperature gradient, and a signal processing section which incorporates sensing data according to the state detected by the sensor section into the spin current generated by the spin current generating section and carries out signal processing.

First Exemplary Embodiment

Figure 1:
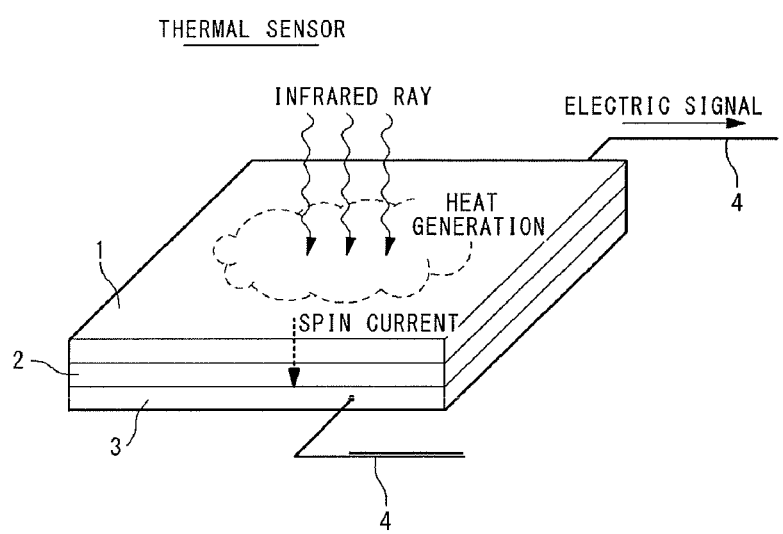
FIG. 1 is a perspective view schematically showing the configuration of a thermal sensor (an infrared sensor) according to a first exemplary embodiment of the present invention.

The thermal sensor according to the first exemplary embodiment of the present invention will be described with reference to the drawings. FIG. 1 is a perspective view schematically showing the configuration of the thermal sensor according to the first exemplary embodiment of the present invention.

The thermal sensor shown in FIG. 1 is an infrared sensor. This thermal sensor has an infrared ray absorption film 1 (a detecting film), a magnetic film 2 and an electrode 3, and these films are laminated in this order from the top film. Two terminals 4 are provided in a separate condition to output an electric current and are connected with the electrode 3. When the infrared rays are incident on the infrared ray absorption film 1, at least a part of the infrared rays is absorbed by the infrared ray absorption film 1 and the heat generation occurs. Thus, the temperature difference (the temperature gradient) occurs in the magnetic film 2 between the side of the infrared ray absorption film 1 and the side of the electrode 3. The spin current is generated in a direction of the temperature gradient in the magnetic film 2 (e.g. a direction perpendicular to the film surface) by the spin Seebeck effect (the effect that the spin current is generated due to the temperature gradient) in the magnetic film 2. The generated spin current is injected to the electrode 3. In the electrode 3, the spin current is converted into the electric current by the reverse spin Hall effect. This electric current is taken out outside as an electrical signal through the terminals 4.

As the infrared ray absorption film 1, the well-known material can be used. For example, by depositing a film such as a gold black (gold superfine particles) film having a high infrared absorption factor, and a nickel chrome alloy film, the infrared ray absorption film 1 can be formed. Besides, by applying a carbon black film, the infrared ray absorption film 1 can be obtained.

As the magnetic film 2, it is desirable to use material with a small heat transfer rate, and especially, magnetic insulator. In order to detect the infrared rays in a high sensitivity by the infrared ray absorption film 1, it is necessary to confine heat in the infrared ray absorption film 1 and maintain the temperature difference between the infrared ray absorption film 1 and the electrode 3 in the magnetic film 2. For example, as the magnetic film 2, the insulator such as YIG (yttrium iron garnet) can be used. The spin current is not scattered by conduction electrons in the insulator. Therefore, the insulator is advantageous from the viewpoint of efficient detection of the spin current in the electrode 3. As the method of forming the magnetic film 2 using YIG, a liquid phase epitaxial method, a pulsed laser ablation method, a sputter method, a MOD (organic metal resolution) method, a sol-gel method and an aerosol deposition method are exemplified. As mentioned above, to detect heat in high sensitively, it is desirable that the heat transfer rate of the magnetic film 2 is smaller. It is desirable from this viewpoint that the method of depositing a polycrystalline or nano-crystalline film of YIG by using the MOD method, the sol-gel method, the aerosol deposition method and so on.

It is desirable to use a material that the reverse spin Hall effect appears efficiently, as the electrode 3. Specifically, the electrode 3 can be formed of Pt, Au, Pd, Ag, Bi or those alloys by depositing them a the sputtering method and so on.

The above multi-layer structure can be formed on an optional substrate and each film thickness can be set according to the use. As an example, the film thickness of the infrared ray absorption film 1 is set to 30 nm, the film thickness of the electrode 3 is set to 200 nm and the film thickness of the magnetic film 2 dm is set to be dm=$\lambda/4n$. Here, $\lambda$ is the wavelength of the infrared ray to be detected and n is the refractive index of the magnetic film 2 at the wavelength. For example, when $\lambda=10$ μm and n=2.2, dm is set to 1.13 μm. By setting the film thickness of the magnetic film 2 according to the wavelength of the infrared ray and the refractive index of the magnetic film 2 at the wavelength, a resonance structure can be formed between the infrared ray absorption film 1 and the electrode 3, and the infrared ray absorption efficiency in the infrared ray absorption film 1 can be improved. Also, because the structure becomes simple compared with a thermopile type sensor (in which many thermocouples are connected in serial to increase an output voltage) by use of the conventional thermoelectric conversion, a multi-layer structure can be formed to have a film structure by using an application technique. Also, this multi-layer structure can be used just as it is, as a thermoelectric conversion device which generates an electric current from the heat.

According to the first exemplary embodiment, the thermal sensor having high sensitivity in the simple structure is obtained by detecting small heat generation by using the degree of freedom of the spin current. In other words, when the insulator material is used as the magnetic film 2, the material with a very small heat transfer rate can be adopted, the temperature gradient due to the heat generation can be maintained, the spin current can be efficiently generated, and the high sensitive detection becomes possible. In addition, when the heat generation is detected by the spin current in the magnetic insulator, it is not necessary to connect electric wirings directly to the heat generation portion. Therefore, the micromachining process can be omitted because it is adiabatic, and the thermal sensor having the high sensitivity in the comparatively simple structure can be obtained, resulting in a low cost.

Second Exemplary Embodiment

Figure 2:
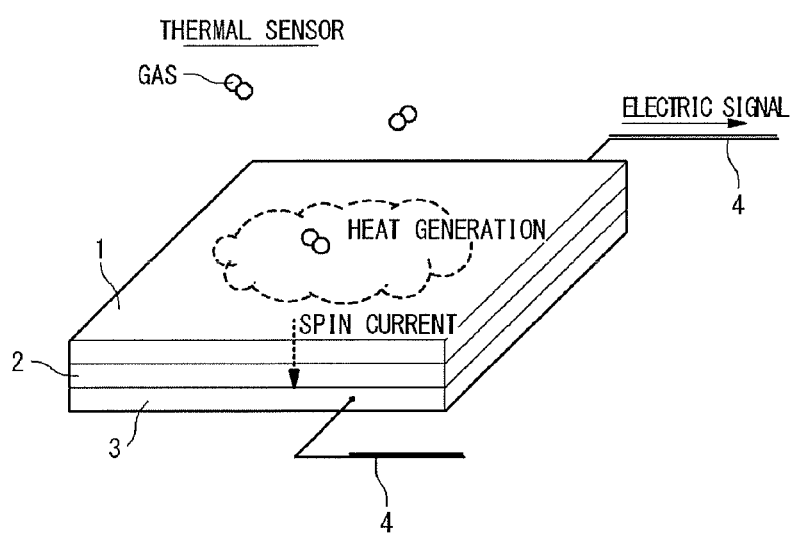
FIG. 2 is a perspective view schematically showing the configuration of the thermal sensor (a gas sensor) according to a second exemplary embodiment of the present invention.

The thermal sensor according to the second exemplary embodiment of the present invention will be described with reference to the drawings. FIG. 2 is a perspective view schematically showing the configuration of the thermal sensor according to the second exemplary embodiment of the present invention.

The thermal sensor shown in FIG. 2 is a gas sensor. The thermal sensor has the electrode 3, the magnetic film 2, and a gas absorption catalyst film 5 (the detecting film), and these films are laminated from the bottom in this order. That is, the thermal sensor has a multi-layer structure. Two terminals 4 are connected with the electrode 3 in a separate condition to take out an electric current. When gas adheres to the gas absorption catalyst film 5, a chemical reaction of gas and the catalyst happens in the gas absorption catalyst film 5, and the gas absorption catalyst film 5 generates heat. Thus, a temperature difference (a temperature gradient) occurs between the gas absorption catalyst film 5 and the electrode 3 in the magnetic film 2. As a result, the spin current is generated in a direction of the temperature gradient (for example, a perpendicular direction to the film surface) due to the spin Seebeck effect in the magnetic film 2. The spin current is injected to the electrode 3. The injected spin current is converted into the electric current by the reverse spin Hall effect in the electrode 3 and is taken out outside through the terminals 4.

As the gas absorption catalyst film 5, the desirable material can be used according to a detection object gas and the well-known material can be used. For example, when the detection object gas is hydrogen, the gas absorption catalyst film 5 can be obtained by forming a platinum (Pt) catalyst film by a sputtering method. Also, as the gas absorption catalyst film 5, the film which contains a porous material which contains the catalyst, and the film which contains a porous material which holds the catalyst can be used.

As the magnetic film 2, it is desirable to use material with a small heat transfer rate and the magnetism insulator is desirable. In order to detect gas in high sensitivity, it is necessary to confine heat in the gas absorption catalyst film 5 and to maintain the temperature difference between the gas absorption catalyst film 5 and the electrode 3 in the magnetic film 2. For example, as the magnetic film 2, an insulator such as YIG (yttrium iron garnet) can be used. Because the spin current is not scattered by the conduction electrons, the insulator is advantageous in the point that the spin current can be detected efficiently in the electrode 3. As a method of forming the magnetic film 2 using YIG, a liquid phase epitaxial method, a pulsed laser ablation method, a sputtering method, a MOD method and a sol-gel method are exemplified. As mentioned above, it is desirable that the heat transfer rate of the magnetic film 2 is smaller in order to detect the heat in high sensitively. From this viewpoint, the method of depositing the nano crystals of YIG by using the sol-gel method is desirable.

As the electrode 3, it is desirable to use the material which the reverse spin Hall effect appears efficiently. The electrode 3 can be obtained by sputtering Pt, Au, Pd, Ag, or Bi or those alloys by the sputtering method.

The above multi-layer structure can be formed on the substrate. The thickness of each of the films of the multi-layer structure can be set according to an application. For example, the film thickness of the infrared ray absorption film 1 is set to 30 nm, the film thickness of the magnetic film 2 is set to 500 nm and the film thickness of the electrode 3 can be set to 200 nm.

According to the second exemplary embodiment, the same effect as the first exemplary embodiment can be attained.

Third Exemplary Embodiment

Figure 3:
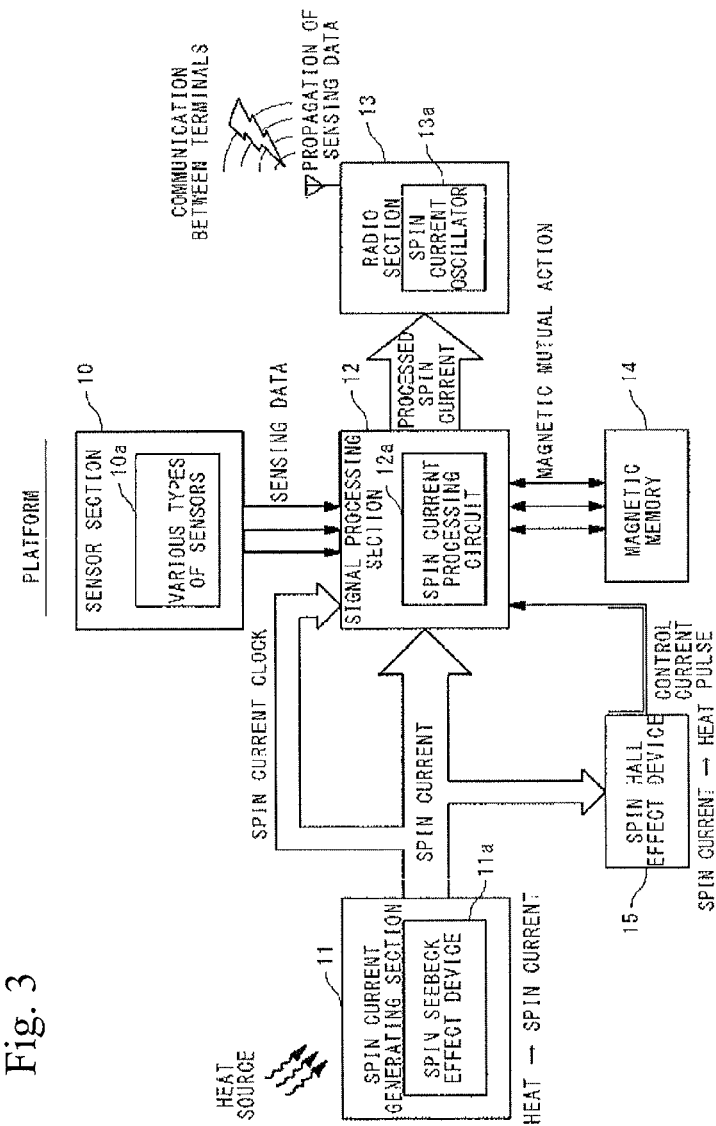
FIG. 3 is a diagram schematically showing the configuration of a platform according to a third exemplary embodiment of the present invention.

The platform according to a third exemplary embodiment of the present invention will be described with reference to the drawings. FIG. 3 is a diagram schematically showing the configuration of the platform according to the present exemplary embodiment.

In the first and second exemplary embodiments, the thermal sensors using the spin current have been described. On the other hand, in the present exemplary embodiment, the platform which drives the sensor using the spin current will be described. The platform shown in FIG. 3 is a radio sensor platform which is driven with the spin current. The platform has a sensor section 10, a spin current generating section 11, a signal processing section 12, a radio section 13, a magnetic memory 14 and a spin Hall effect device 15.

As mentioned later, the sensor section 10 has a sensor 10a which detects various conditions. For example, as the sensor 10a, the infrared sensor according to the first exemplary embodiment, the thermal sensor according to the second exemplary embodiment, and other sensors such as the gas sensor can be used. The sensor section 10 outputs sensing data showing the detected condition to the signal processing section 12. Because there are some methods as a method of inputting data to the signal processing section 12 as mentioned later, the sensing data may be outputted as an electric signal or a magnetic signal. For example, the sensing data can be superposed on a voltage signal.

The spin current generating section 11 is used as a power supply to various functional sections. The spin current generating section 11 has a function to collect energy from the periphery and has a spin Seebeck effect device 11a which generates a spin current thermally from a spatial temperature gradient. In the spin current generating section 11, the spin Seebeck effect device 11a generates the spin current from the peripheral heat. The generated spin current is outputted to the signal processing section 12 and the spin Hall effect device 15. The detailed configuration and operation of the spin current generating section 11 will be described later.

The signal processing section 12 has a function to carry out information processing to an inputted signal. The signal processing section 12 has a spin current processing circuit 12a. The spin current processing circuit 12a reflects the sensing data on the phase of the spin current generated by the spin current generating section 11, and carries out the information processing (integration, arrangement, encryption and so on of data). The signal processing section 12 outputs data subjected to the information processing to the radio section 13 as a processed spin current. The signal processing section 12 superimposes a storage content of the magnetic memory 14 on the phase of the spin current through magnetic interaction. The signal processing section 12 may perform the signal processing by using the spin current generated by the spin current generating section 11 as a clock. The signal processing section 12 may carry out the signal processing by using a control current pulse generated by the spin Hall effect device 15. The detailed configuration and operation of the signal processing section 12 will be described later.

The radio section 13 has a spin current oscillator 13a. When the processed spin current is acquired from the signal processing section 12, the spin current oscillator 13a generates microwave. In the radio section 13, the generated microwave is transmitted to a base station and a neighboring terminal. The detailed configuration and operation of the radio section 13 will be described later.

The magnetic memory 14 has a function to store data such as measurement data of the sensor section 10 and ID data magnetically. The magnetic memory 14 can store and read data according to the signal processing by the signal processing section 12.

The spin Hall effect device 15 is a device which generates an electric current from the spin current generated by the spin current generating section 11. The spin Hall effect device 15 outputs a generated electric current to the signal processing section 12 as a control electric current pulse.

Hereinafter, each section in the platform shown in FIG. 3 will be described in detail.

Figure 4:
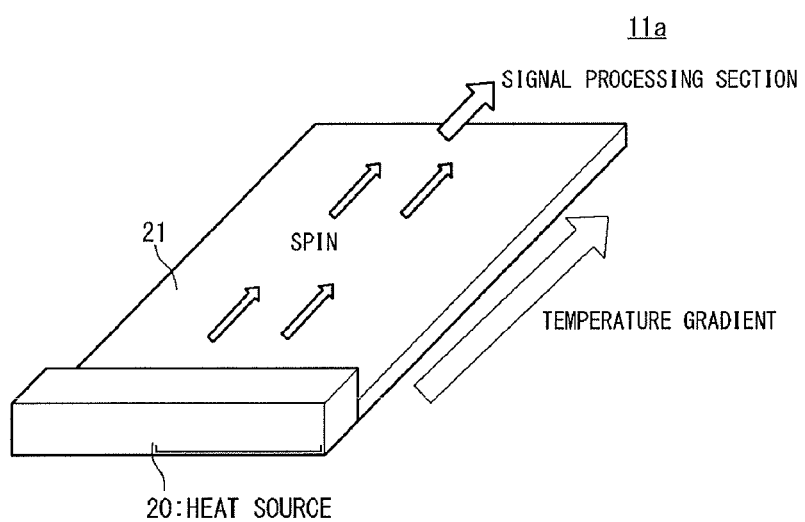
FIG. 4 is a perspective view schematically showing the structure of the spin Seebeck device.

The spin current generating section 11 functioning as the power supply of the platform will first be described. AS mentioned previously, the spin current generating section 11 is provided with the spin Seebeck effect device 11a. Also, the spin current generating section 11 is connected with the signal processing section 12 through the spin current waveguide 21. FIG. 4 is a perspective view schematically showing the structure of the spin Seebeck effect device 11a.

The spin Seebeck effect device 11a is a device which generates the spin current from the heat by using the spin Seebeck effect. For example, the spin Seebeck effect is mentioned in Patent Literature 3 (JP 2009-130070A). As shown in FIG. 4, the spin Seebeck effect device 11a is provided as an end or part of the spin current waveguide 21. The spin Seebeck effect device 11a is arranged in the neighborhood to the hot or cold heat source 20. Thus, the temperature gradient occurs in the spin current waveguide 21 and the spin current is generated by the spin Seebeck effect. As the heat source 20, the heat source may be used such as the heat source 20, solar heat, body temperature, and various types of waste heat. The generated spin current is transmitted to the signal processing section 12 (FIG. 3) through the spin current waveguide 21.

It is required that the material for the spin current waveguide 21 is a magnetic substance. It is desirable that as the magnetic substance body, an insulator material is used in which the dissipation is small even if the propagation distance of the spin current is long, as described in Patent Literature 3. For example, as the magnetic substance, the magnetic material of the garnet system can be used.

Figure 5:
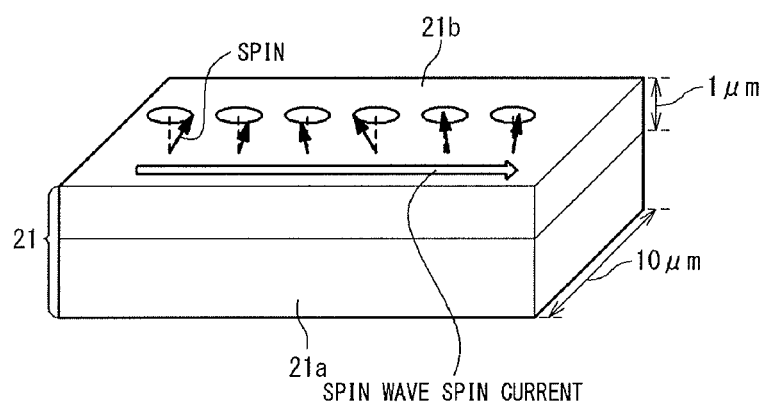
FIG. 5 is a perspective view showing an application example of the spin Seebeck device.

FIG. 5 is a perspective view showing a specific application example of the spin Seebeck effect device 11a, and is a perspective view showing a state that a spin wave spin current is propagated through the spin current waveguide 21. For example, the spin current waveguide 21 can be made as follows.

First, a GGG substrate 21a of gadolinium gallium garnet (GGG) is prepared (FIG. 5). By a liquid phase epitaxy (LPE) and a pulsed laser ablation deposition (PLD) method, a single crystal film of yttrium iron garnet (YIG) is deposited on the GGG substrate 21a as a YIG film 21b having the film thickness of about 1 μm. Thus, the spin current waveguide 21 is obtained. When the spin current waveguide 21 is formed of the insulator such as YIG, the spin current to be transmitted through it becomes a spin wave spin current which has the frequency of GHz order (Patent Literature 3). The spin wave spin current in which a fluctuation of the spin is propagated through the magnetic interaction is as shown in FIG. 5. For example, the film thickness of YIG film 21b is 1 μm and the width of the spin current waveguide is 10 μm.

Figure 6A:
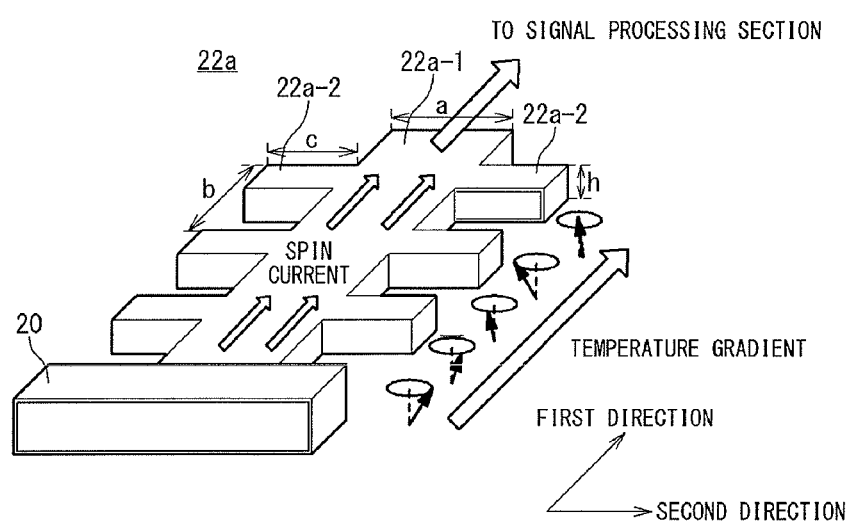
FIG. 6A is a perspective view schematically showing a spin Seebeck device in which a waveguide width is periodically modulated.
Figure 6B:
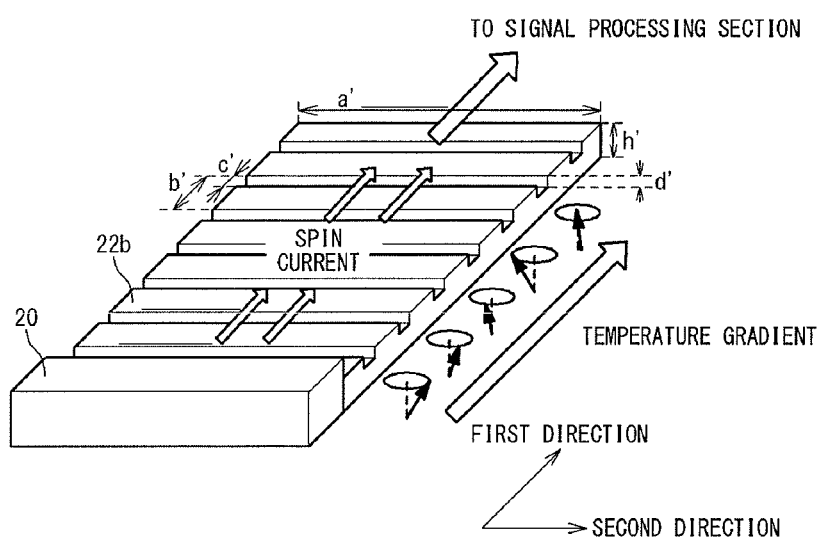
FIG. 6B is a perspective view showing the structure of the spin Seebeck device in which a periodic ditch is formed on the waveguide surface.
Figure 6C:
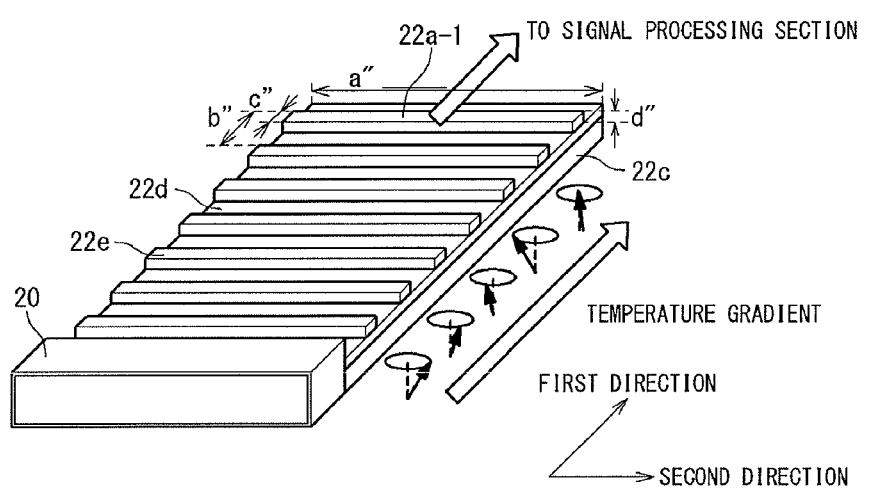
FIG. 6C is a perspective view showing the structure of the spin Seebeck device which a ferromagnetic material film is periodically formed.

FIG. 6A to FIG. 6C are perspective views schematically showing other application examples of the spin Seebeck effect device 11a. FIG. 6A is a perspective view showing a spin Seebeck effect device in which an application example showing waveguide width is periodically modulated. FIG. 6B is a perspective view showing a spin Seebeck effect device in which periodic ditches are provided on the surface of the waveguide. FIG. 6C is a perspective view showing the spin Seebeck effect device in which ferromagnetic films are periodically formed on the waveguide surface through a barrier layer.

The spin wave spin current which is generated based on the temperature gradient has various frequency modes. However, by devising the configuration of the spin Seebeck effect device, the spin wave spin current to be propagated can be controlled. For example, as shown in FIG. 6A and FIG. 6B, it is possible to control the spin wave spin current to be propagated by using the spin current waveguide 22a or 22b of a period structure in which width and height are periodically modulated, as the spin Seebeck effect device. Also, as shown in FIG. 6C, it is possible to control the spin wave spin current to be propagated by using the spin current waveguide 22c in which a periodic ferromagnetic film 22e is formed on the surface through a barrier layer 22d, as the spin Seebeck effect device. If designing appropriately, the spin wave spin current which has a single frequency can be supplied to the signal processing section (FIG. 3). The configuration of the spin current waveguide shown in FIG. 6A to FIG. 6C will be described below.

The spin current waveguide 22a shown in FIG. 6A is provided with a trunk section 22a-1 and a plurality of branch sections 22a-2. The trunk section 22a-1 extends along a first direction and is connected with the heat source 20 at one end. Each of the plurality of branch sections 22a-2 extends along a second direction which is orthogonal to the first direction and extends on the both sides from the trunk section 22a-1. In the first direction, the plurality of branch sections 22a-2 are arranged every distance "b". That is, the width of the spin current waveguide 22a in the second direction changes periodically. The thickness of the spin current waveguide 22a is "h". Also, the width of the trunk section 22a-1 in the second direction is "a". The length of each branch section 22a-2 in the second direction is "c". By setting these parameters "a", "b", "c" and "h" to suitable values, the frequency of the propagating spin wave spin current can be controlled.

The spin current waveguide 22b shown in FIG. 6B extends in the first direction and is connected with the heat source 20 at one end. Also, a plurality of ditches extending in the second direction (a direction orthogonal to the first direction) are formed on the spin current waveguide 22b. The width of the spin current waveguide 22b in the second direction is "a'". The thickness of the spin current waveguide 22b is "h'". Each width (the width in the first direction) of the plurality of ditches is "c'". The depth of each ditch is "d'". In the first direction, the plurality of ditches are arranged every distance "b'". By setting parameters "a'", "h'", "c'", "d'" and "b'" to suitable values, the frequency of the propagating spin wave spin current can be controlled.

The spin current waveguide 22c shown in FIG. 6C extends along the first direction. The width of the spin current waveguide 22c in the second direction is "a''". The barrier layer 22d is provided for the surface of the spin current waveguide 22c. The thickness of the barrier layer 22d is "d''". The plurality of ferromagnetic films 22e are formed on the barrier layer 22d. Each ferromagnetic film 22e extends along the second direction. The width (the width in the first direction) of each ferromagnetic film 22a is "c''". The plurality of ferromagnetic films 22a are arranged every distance "b''" in the first direction. By setting these parameters "a''", "d''", "c''" and "b''" to suitable values, the frequency of the propagating spin wave spin current can be controlled.

Next, the signal processing section 12 will be described. The signal processing section 12 is realized by combining spin current branching devices, spin current combining devices, spin current partial reflection mirrors, and spin current modulators.

Figure 7A:
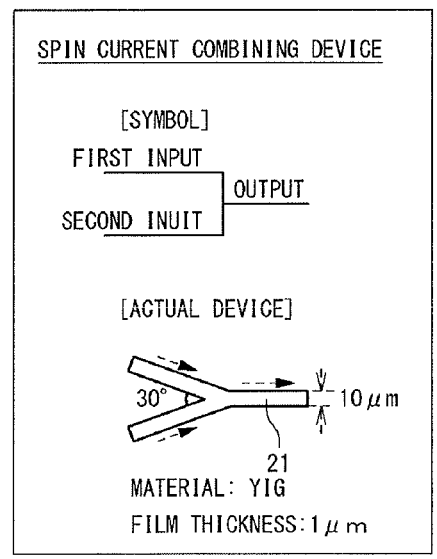
FIG. 7A is a diagram schematically showing the spin current combining device.
Figure 7B:
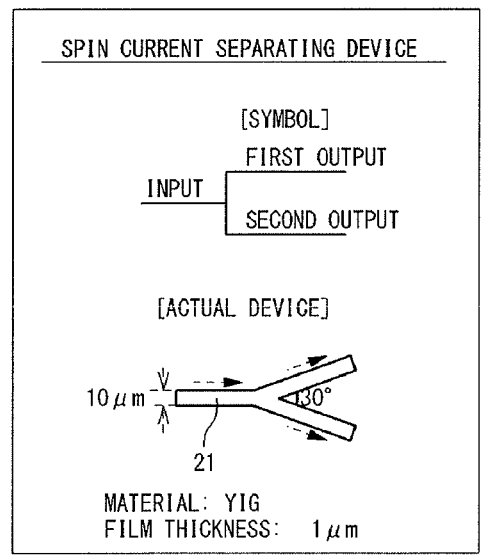
FIG. 7B is a diagram schematically showing a spin current branching device.
Figure 8A:
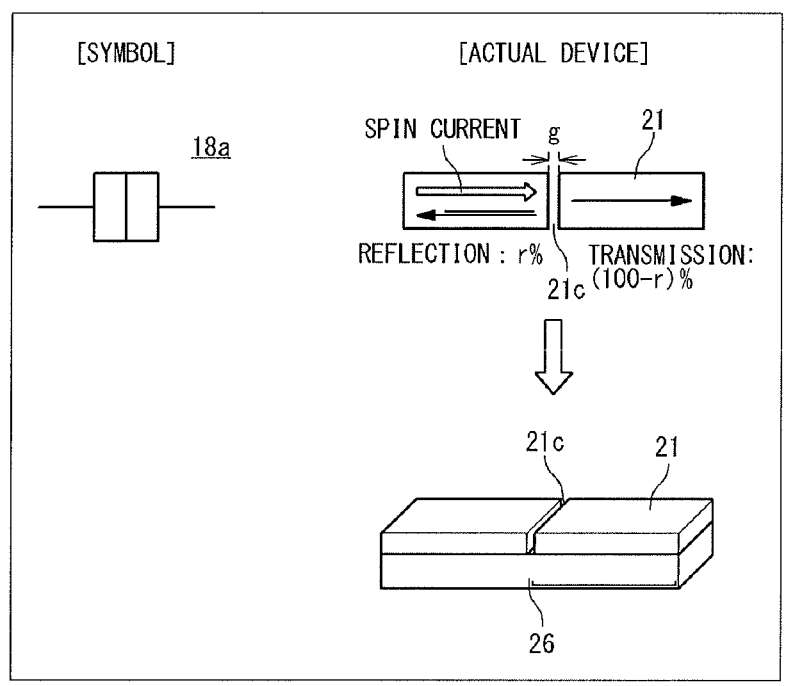
FIG. 8A is a diagram schematically showing an example of a 2-terminal type spin current partial reflection mirror using a gap.
Figure 8B:
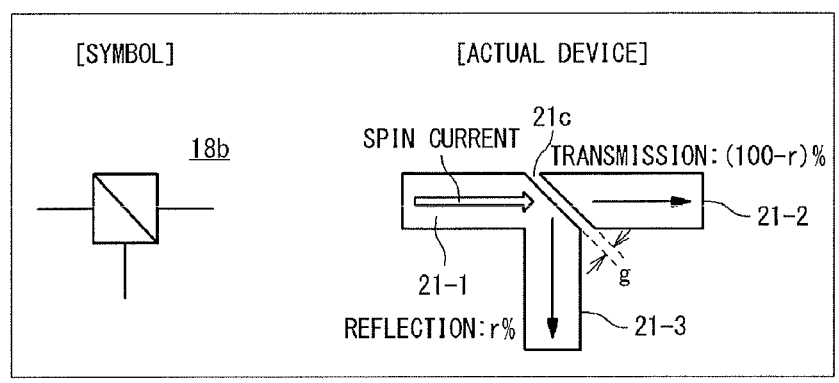
FIG. 8B is a diagram schematically showing an example of a 3-terminal type spin current partial reflection mirror using a gap.
Figure 8C:
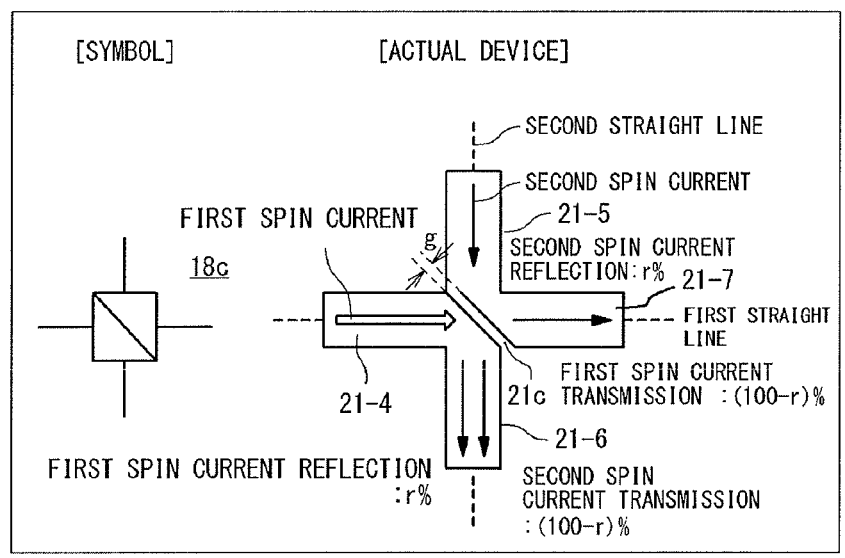
FIG. 8C is a diagram schematically showing an example of a 4-terminal type spin current partial reflection mirror using a gap.

FIG. 7A is a diagram schematically showing the spin current combining device. FIG. 7B is a diagram schematically showing the spin current branching device. FIG. 8A to FIG. 8C are diagrams schematically showing examples of the spin current partial reflection mirrors using a small gap.

FIG. 8A shows the spin current partial reflection mirror of a 2-terminal type. FIG. 8B shows the spin current partial reflection mirror of a 3-terminal type. FIG. 8C shows the spin current partial reflection mirror of a 4-terminal type.

Figure 9A:
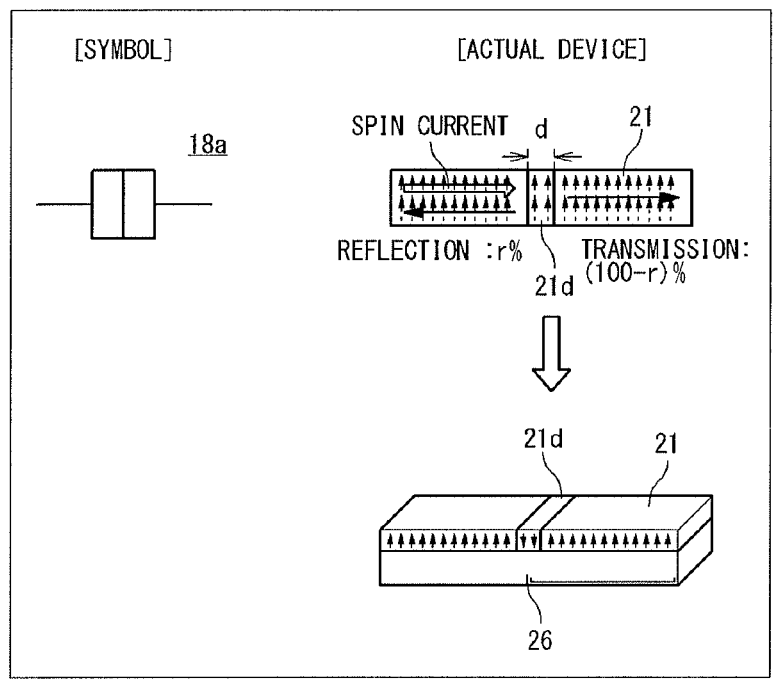
FIG. 9A is a diagram schematically showing an example of the 2-terminal type spin current partial reflection mirror using a domain wall.
Figure 9B:
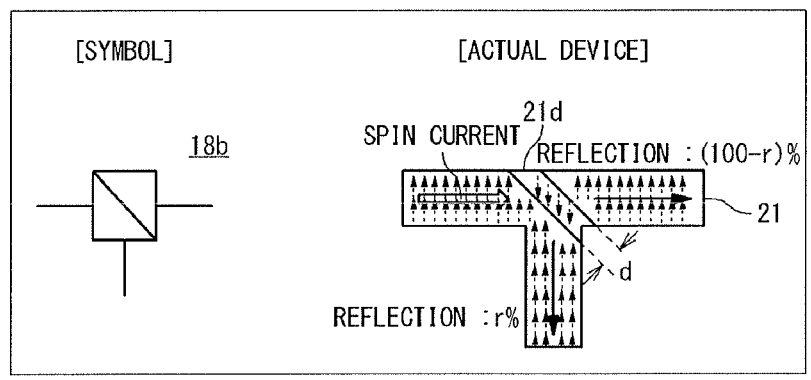
FIG. 9B is a diagram schematically showing an example of a 3-terminal type spin current partial reflection mirror using a domain wall.
Figure 9C:
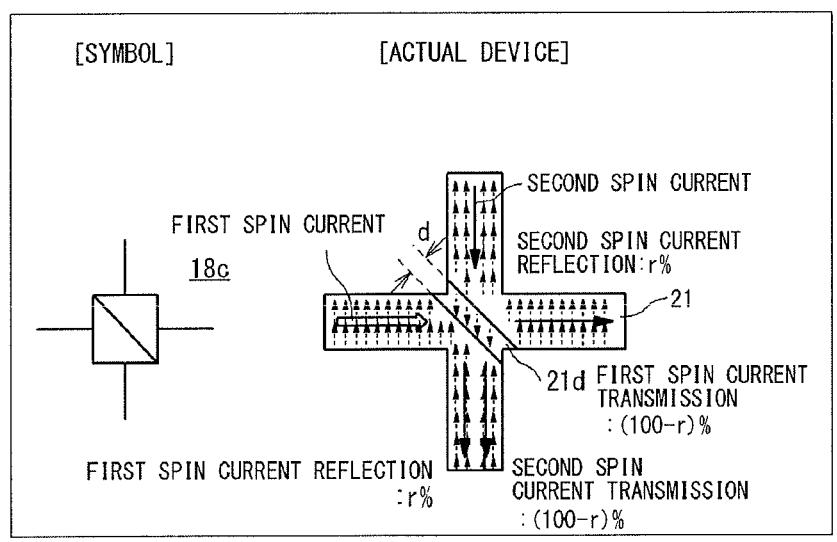
FIG. 9C is a diagram schematically showing an example of a 4-terminal type spin current partial reflection mirror using a domain wall.

FIG. 9A to FIG. 9C are diagrams schematically showing the spin current partial reflection mirrors using a domain wall structure. FIG. 9A shows the spin current partial reflection mirror of the 2-terminal type. FIG. 9B shows the spin current partial reflection mirror of the 3-terminal type. FIG. 9C shows the spin current partial reflection mirror of the 4-terminal type.

Figure 10A:
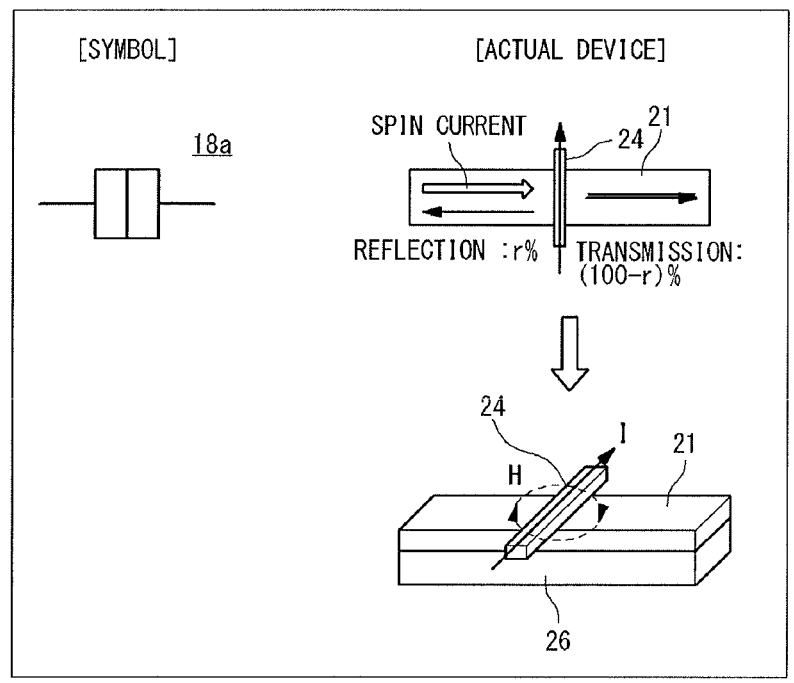
FIG. 10A is a diagram schematically showing an example of a 2-terminal type spin current partial reflection mirror using an external magnetic field.
Figure 10B:
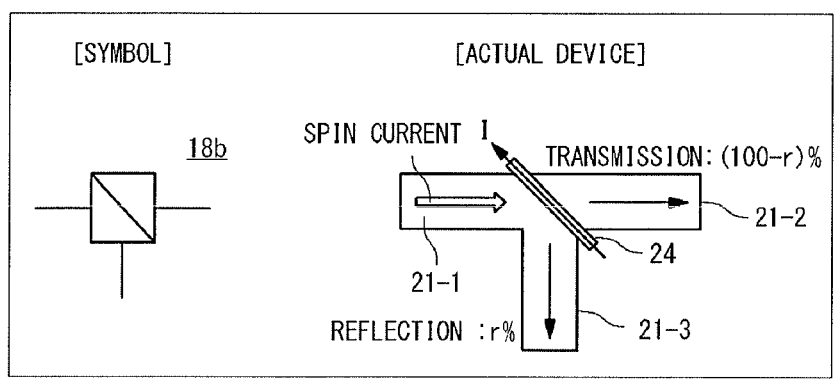
FIG. 10B is a diagram schematically showing an example of a 3-terminal type spin current partial reflection mirror using an external magnetic field.
Figure 10C:
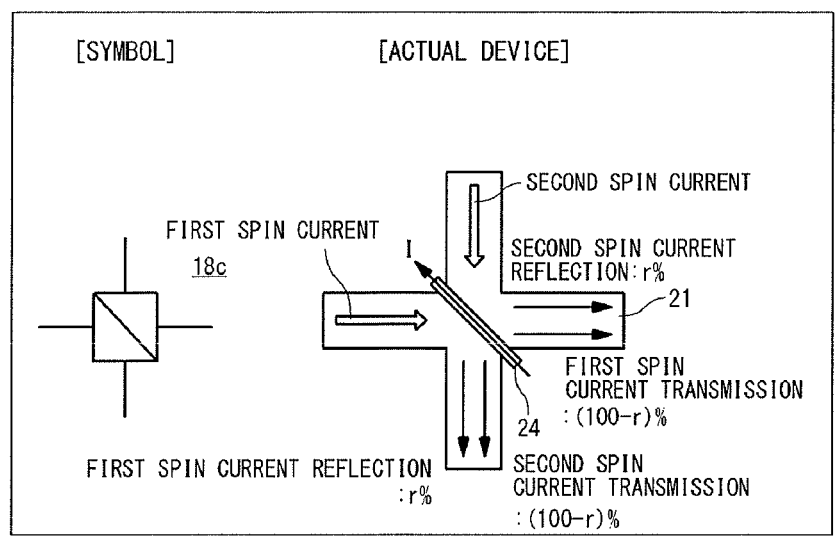
FIG. 10C is a diagram schematically showing an example of a 4-terminal type spin current partial reflection mirror using an external magnetic field.

FIG. 10A to FIG. 10C are diagrams schematically showing the spin current partial reflection mirrors using external magnetic field. FIG. 10A shows the spin current partial reflection mirror of the 2-terminal type. FIG. 10B shows the spin current partial reflection mirror of the 3-terminal type. FIG. 10C show the spin current partial reflection mirror of the 4-terminal type.

Figure 11A:
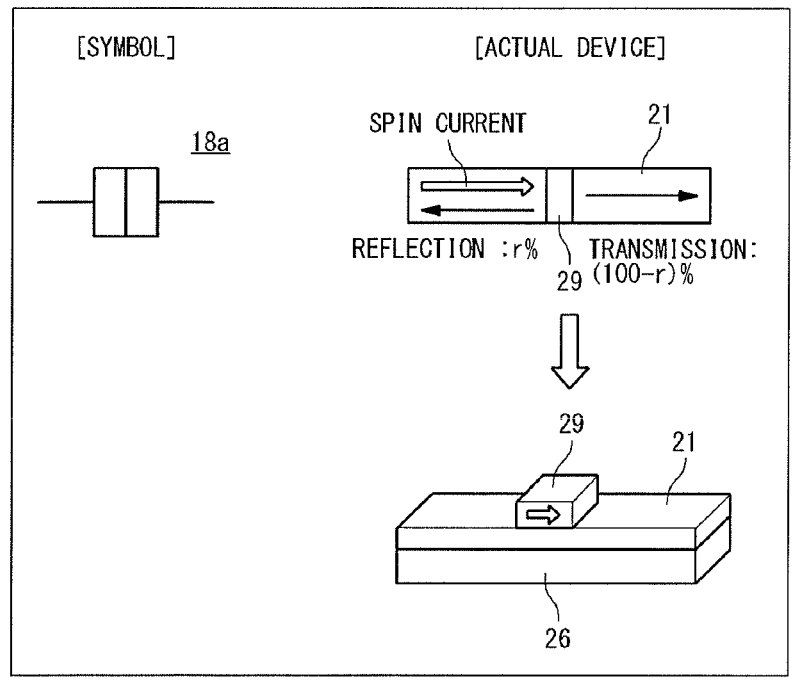
FIG. 11A is a diagram schematically showing an example of a 2-terminal type spin current partial reflection mirror using a magnetic terminal.
Figure 11B:
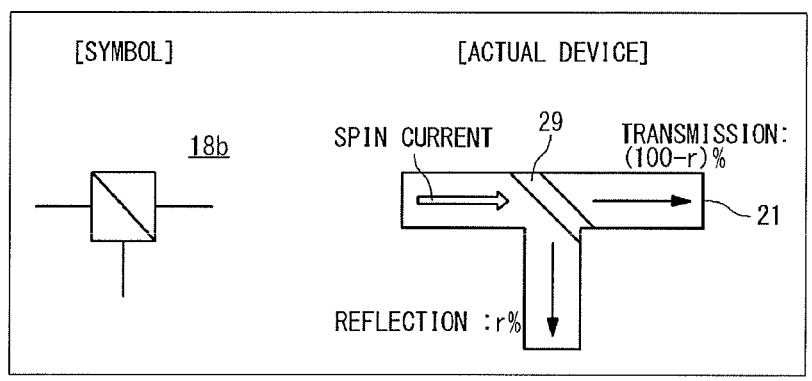
FIG. 11B is a diagram schematically showing an example of a 3-terminal type spin current partial reflection mirror using a magnetic terminal.
Figure 11C:
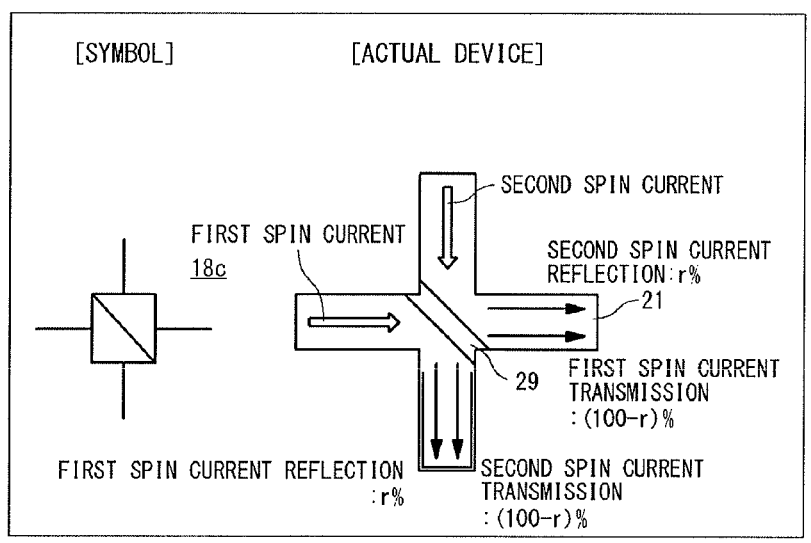
FIG. 11C is a diagram schematically showing an example of a 4-terminal type spin current partial reflection mirror using a magnetic terminal.

FIG. 11A to FIG. 11C are diagrams schematically showing the spin current partial reflection mirror using a magnetic terminal. FIG. 11A shows the spin current partial reflection mirror of the 2-terminal type. FIG. 11B shows the spin current partial reflection mirror of the 3-terminal type. FIG. 11C shows the spin current partial reflection mirror of the 4-terminal type.

Figure 12A:
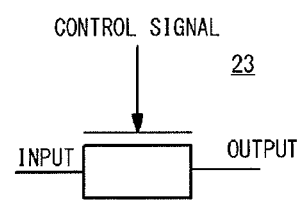
FIG. 12A is a diagram showing the spin current modulator.
Figure 12B:
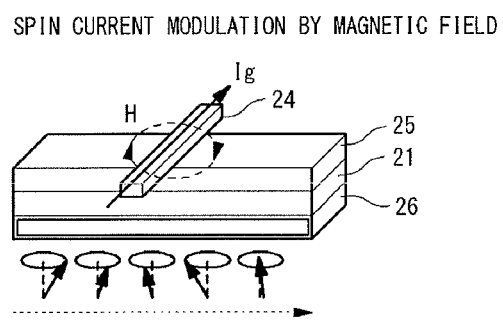
FIG. 12B is a diagram schematically showing the spin current modulator using magnetic field.
Figure 12C:
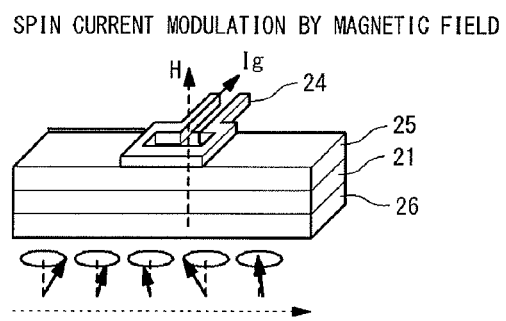
FIG. 12C is a diagram schematically showing another spin current modulator using magnetic field.
Figure 12D:
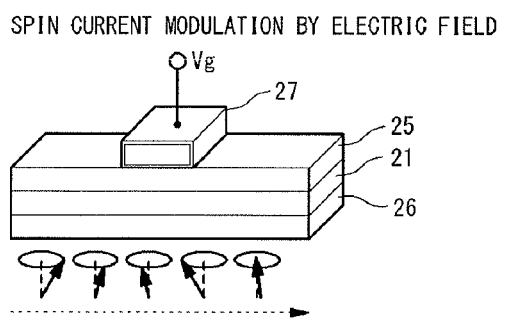
FIG. 12D is a diagram schematically showing the spin current modulator using electric field.
Figure 12E:
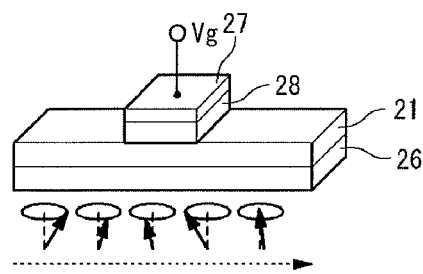
FIG. 12E is a diagram schematically showing the spin current modulator using strain.
Figure 12F:
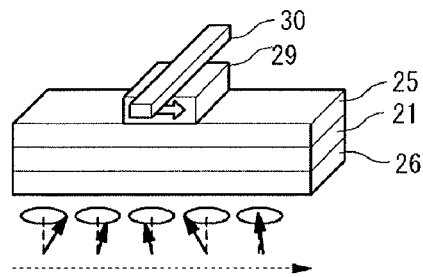
FIG. 12F is a diagram schematically showing the spin current modulator using a magnetic terminal.

FIG. 12A to FIG. 12F are diagrams schematically showing the spin current modulators. FIG. 12A shows the spin current modulator using magnetic field. FIG. 12B shows another spin current modulator using magnetic field. FIG. 12C shows the spin current modulator using electric field. FIG. 12D shows the spin current modulator using strain. FIG. 12E shows the spin current modulator using a magnetic device. FIG. 12F shows the spin current modulator using a domain wall.

First, the spin current branching device, the spin current combining device, the spin current partial reflection mirror and the spin current modulator will be described. These devices are devices which realize the basic functions of the signal processing by the spin current.

As shown in FIG. 7A, in the spin current combining device, two spin current waveguides 21 for input are connected with one spin current waveguide 21 for output. Thus, the combination of the spin currents becomes possible. Also, as shown in FIG. 7B, in the spin current branching device, one spin current waveguide 21 for input is branched to two spin current waveguides 21 for output. Thus, while the phase data is kept, it is possible to branch the spin current. For example, the width of the spin current waveguide 21 is 10 μm. For example, the film thickness in the spin current waveguide 21 is 1 μm. For example, an angle at the combining portion or the branching portion is 30°. Also, three or more spin current waveguides 21 can be combined in the same way and it is possible to branch to them. As the material of the spin current waveguide 21, YIG can be used.

Also, by designing appropriately, the spin current partial reflection mirror can be configured to reflect the spin current partially in an optional reflectivity. FIG. 8A to FIG. 8C are diagrams showing examples of the spin current partial reflection mirrors using a small gap.

FIG. 8A is a diagram showing an application example of the 2-terminal type spin current partial reflection mirror 18a and a symbol. The 2-terminal type spin current partial reflection mirror 18a has a spin current waveguide 21 formed on a substrate 26 and a gap 21c which cut off the spin current waveguide 21. The width of the gap 21c is "g". By providing the gap 21c, a part (r %) of the spin current is reflected to back (input side). On the other hand, a remaining part ((100−r) %) of the spin current passes though (tunnels) the gap 21c and advances to a front direction (the side of the output) by the magnetic interaction. By adjusting the gap width "g", a desired value can be obtained as reflectivity "r". It should be noted that the insulator barrier film (e.g. $SiO_2$ film) may be buried in the gap 21c.

FIG. 8B is a diagram showing an application example of the 3-terminal type spin current partial reflection mirror 18b and a symbol. In the 3-terminal type spin current partial reflection mirror 18b, the spin current waveguide 21 has an input section 21-1, an output section 21-2 and an output section 21-3. The input section 21-1 and the output section 21-2 are provided onto an identical straight line. The gap 21c is provided between the input section 21-1 and the output section 21-2. The gap 21c extends diagonally to a direction in which the input section 21-1 extends and cut off between the input section 21-1 and the output section 21-2. The output section 21-3 is connected to a tip of the input section 21-1. The output section 21-3 extends in a direction orthogonal to the direction of the input section 21-1 from the tip of the input section 21-1. Specifically, the output section 21-3 extends in a direction where the spin wave reflected by the gap 21c is propagated. In the 3-terminal spin current partial reflection mirror 18b, the spin current advances toward the output section 21-2 through the input section 21-1. A part of the spin current passes through the gap 21c and is led to the output section 21-2. On the other hand, the other part of the spin current is reflected by the gap 21c and is led to the output section 21-3.

FIG. 8C is a diagram showing an application example of the 4-terminal type spin current partial reflection mirror 18c and a symbol. In the 4-terminal type spin current partial reflection mirror 18c, the spin current waveguide 21 is provided with two input sections (an input section 21-4, an input section 21-5) and two output sections (an output section 21-6, an output section 21-7). The input section 21-4 and the output section 21-7 are provided onto a first straight line. The input section 21-5 and the output section 21-6 are provided onto a second straight line. The first straight line and the second straight line are orthogonal to each other. The gap 21c is provided for an intersection point of the first straight line and the second straight line. The gap 21c extends diagonally to both of the first straight line and the second straight line. The input section 21-4 and the output section 21-6 are cut off from the input section 21-5 and the output section 21-7 by the gap 21c. By adopting such a configuration, two spin currents advancing to directions orthogonal to each other can be mixed (interfered) in a rate which is determined with the reflectivity "r".

By using a domain wall instead of the gap 21c in the 2-terminal type spin current partial reflection mirror shown in FIG. 8A, the spin current partial reflection mirror having a similar function can be realized.

FIG. 9A is a diagram showing the 2-terminal type spin current partial reflection mirror 18a using a domain wall and a symbol. In the 2-terminal type spin current partial reflection mirror 18a shown in FIG. 9A, the domain wall 21d is provided instead of the gap 21c. The other points are the same as the spin current partial reflection mirror shown in FIG. 8A. In the 2-terminal type spin current partial reflection mirror 18a, a part (r %) of the inputted spin current is reflected by the domain wall 21d. On the other hand, a remaining part ((100−r) %) of the inputted spin current passes through the domain wall 21d and advances forward. Also, the 3-terminal type spin current partial reflection mirror 18b and the 4-terminal type spin current partial reflection mirror 18c can be realized by using the domain wall as shown in FIG. 8B and FIG. 8C.

FIG. 9B is a diagram showing the 3-terminal type spin current partial reflection mirror 18b using a domain wall and a symbol. In the 3-terminal type spin current partial reflection mirror 18b shown in FIG. 9B, the domain wall 21d is provided instead of the gap 21c. The other points are the same as those of the 3-terminal type spin current partial reflection mirror shown in FIG. 8B.

FIG. 9C is a diagram showing the 4-terminal type spin current partial reflection mirror 18c using a domain wall and a symbol. In the 4-terminal type spin current partial reflection mirror 18c shown in FIG. 9C, the domain wall 21d is provided instead of the gap 21c. The other points are the same as the 4-terminal type spin current partial reflection mirror shown in FIG. 8C.

Also, it is possible to realize the spin current partial reflection mirror by using a small external magnetic field. FIG. 10A is a diagram schematically showing the 2-terminal type spin current partial reflection mirror 18a using the external magnetic field and a symbol. The 2-terminal type spin current partial reflection mirror 18a is provided with the spin current waveguide 21 and magnetic field applying terminal 24. The magnetic field applying terminal 24 is provided onto the spin current waveguide 21 and extends to cross the spin current waveguide 21. The magnetic field applying terminal 24 is configured such that electric current I flows through the magnetic field applying terminal 24. Moreover, in the 2-terminal type spin current partial reflection mirror 18a using the external magnetic field, when the electric current I is applied to the magnetic field applying terminal 24, a local magnetic field H is generated in a directly beneath portion of the magnetic field applying terminal 24. As a result, the change of the potential occurs in the spin current waveguide 21. A part of the spin current flowing through the spin current waveguide 21 is reflected in the potential change part. The remaining part of the spin current passes through the potential change part. In this way, the same function as the 2-terminal type spin current partial reflection mirror 18a shown in FIG. 8A is realized.

Also, like examples shown in FIG. 8B and FIG. 8C, the 3-terminal type spin current partial reflection mirror 18b and the 4-terminal type spin current partial reflection mirror 18c can be realized by using a local external magnetic field. FIG. 10B is a diagram showing the 3-terminal type spin current partial reflection mirror 18b using the external magnetic field and a symbol. Differing from the 3-terminal type spin current partial reflection mirror 18b shown in FIG. 8B, in the 3-terminal type spin current partial reflection mirror 18b, the gap

21c is not provided. Instead, the magnetic field applying terminal 24 is provided on the spin current waveguide 21 in the position corresponding to the gap 21c. The other points are the same as those of the 3-terminal type spin current partial reflection mirror 18b shown in FIG. 8B.

Also, FIG. 10C is a diagram showing the 4-terminal type spin current partial reflection mirror 18c using the external magnetic field and a symbol. Differing from the 4-terminal type spin current partial reflection mirror 18c shown in FIG. 8C, in the 4-terminal type spin current partial reflection mirror 18c, the gap 21c is not provided. Instead, the magnetic field applying terminal 24 is provided on the spin current waveguide 21 in the position corresponding to the gap 21c. The other points are the same as those of the 4-terminal type spin current partial reflection mirror 18c shown in FIG. 8C.

FIG. 11A to FIG. 11C are diagrams showing the spin current partial reflection mirrors 18a, 18b, and 18c using magnetic terminals 29. FIG. 11A is a diagram showing the 2-terminal type spin current partial reflection mirror 18a and a symbol. In the spin current partial reflection mirror 18a shown in FIG. 11A, the magnetic terminal 29 is provided in place of the magnetic field applying terminal 24 (FIG. 10A). The other points are same as those of the spin current partial reflection mirror 18a shown in FIG. 10A.

FIG. 11B is a diagram showing the 3-terminal type spin current partial reflection mirror 18b and a symbol. The magnetic terminal 29 is provided in place of the magnetic field applying terminal 24 (FIG. 10B) in the spin current partial reflection mirror 18b shown in FIG. 11B, too. The other points are the same as the spin current partial reflection mirror 18b shown in FIG. 11B.

FIG. 11C is a diagram showing the 3-terminal type spin current partial reflection mirror 18c and a symbol. In the spin current partial reflection mirror 18c shown in FIG. 11C, the magnetic terminal 29 is provided in place of the magnetic field applying terminal 24 (FIG. 10C). The other points are the same as those of the spin current partial reflection mirror 18c shown in FIG. 10C.

As shown in FIG. 11A to FIG. 11C, the spin current partial reflection mirrors 18 can be realized by arranging the magnetic terminal 29 on the spin current waveguide 21. By providing the magnetic terminal 29, it is possible to generate a small potential change in the spin current waveguide 21. As a result, a part of the spin current is reflected in a small potential change portion. The remaining part of the spin current passes through the small potential change portion.

Next, the spin current modulator will be described. The spin current modulator is a device to shift a phase of the spin wave spin current and is an important element to realize signal processing of the spin current. FIG. 12A is a diagram showing a symbol which expresses the spin current modulator. A control signal is supplied to the spin current modulator and the phase of the spin wave spin current is shifted in response to the control signal. FIG. 12B to FIG. 12G are diagrams showing specific instances of the spin current modulator.

FIG. 12B shows an example of the spin current modulator using a magnetic field applying electrode 24. In the spin current modulator, the magnetic field applying electrode 24 is provided on the spin current waveguide 21 through a barrier film 25. The magnetic field applying electrode 24 extends to cross the spin current waveguide 21. In the spin current modulator, electric current Ig is applied to the magnetic field applying electrode 24 as the control signal. In this way, magnetic field H is generated in the neighborhood of the magnetic field applying electrode 24, and the magnetic field H is applied to the spin current waveguide 21. Thus, by applying external magnetic field, the dispersion of the spin wave spin current (i.e. refractive index) can be controlled (Non-Patent Literature 1). As a result, the phase of the spin wave spin current can be shifted in the spin current waveguide 21.

FIG. 12C shows another example of the spin current modulator using the magnetic field applying electrode 24. In the spin current modulator, the shape of the magnetic field applying electrode 24 is devised such that the magnetic field H to is generated in a direction orthogonal to a plane on which the spin current waveguide 21 is provided. The other points are the same as those of the spin current modulator shown in FIG. 12B. Even if such a configuration is adopted, the phase of the spin wave spin current can be shifted.

FIG. 12D is a diagram showing an example of the spin current modulator using an electric field. In the spin current modulator, a gate electrode 27 is provided on the spin current waveguide 21 through the barrier film 25. A control signal is supplied to the gate electrode 27. The electric field Vg is applied by the gate electrode 27. Even if such a configuration is adopted, the phase of the spin wave spin current can be shifted in the spin current waveguide 21.

FIG. 12E is a diagram showing an example of the spin current modulator using a strain. IN the spin current modulator, the gate electrode 27 is arranged through a piezoelectrical film 28 (PZT, and so on,) on the spin current waveguide 21. A control signal is supplied to the gate electrode 27. The electric field Vs is applied from the gate electrode 27 to cause the strain. Thus, the phase of the spin wave spin current can be shifted in the spin current waveguide 21.

FIG. 12F is a diagram showing an example of the spin current modulator using a magnetic device. In the spin current modulator, the magnetic terminal 29 is provided on the spin current waveguide 21 through the barrier film 25. The reconfiguration electrode 30 is provided on the magnetic terminal 29. The distance between the magnetic terminal 29 and the spin current waveguide 21 is sufficiently close to each other. In the spin current modulator, a control signal is supplied to the magnetic terminal 29. The magnetic interaction occurs between the magnetic terminal 29 and the spin wave spin current which flows through the spin current waveguide 21. Through the magnetic interaction, the phase of the spin wave spin current can be shifted. In this case, a phase shift amount depends on the direction of the magnetization of the magnetic terminal 29. The magnetization of the magnetic terminal 29 can be reconfigured by applying an electric current to the reconfiguration electrode 30.

Figure 12G:
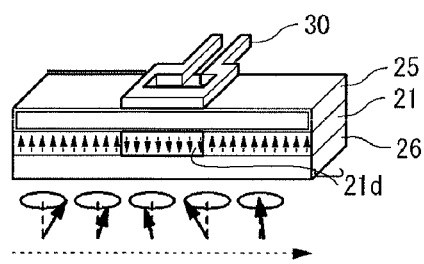
FIG. 12G is a diagram schematically showing the spin current modulator using a domain wall.

FIG. 12G is a diagram showing an example of the spin current modulator using a domain wall. In the spin current modulator, the domain wall 21d is provided in the spin current waveguide 21. Also, the reconfiguration electrode 30 is provided on the spin current waveguide 21 through the barrier film 25. The reconfiguration electrode 30 is provided in the position corresponding to the domain wall 21d. A control signal is supplied to the reconfiguration electrode 30. The phase of the spin wave spin current shifts when passing through the domain wall 21d. By adopting the configuration as shown in FIG. 12G, the phase of the spin wave spin current can be shifted. Also, the generation and extinguishment of the domain wall can be controlled by applying an electric current to the reconfiguration electrode 30 and the reconfiguration of the domain wall 21d becomes possible.

Next, a basic circuit (sensing data taking-in circuit) in which the signal processing section 12 (FIG. 3) takes the sensing data therein and carries out signal processing will be described. The basic circuit is realized by combining the above mentioned basic elements (the spin current branching device, the spin current combining device, the spin current partial reflection mirror, the spin current modulator and so on).

Figure 13:
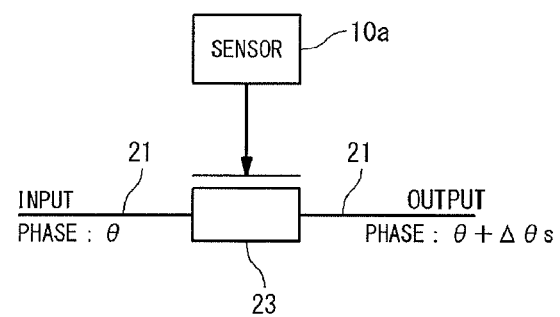
FIG. 13 is a circuit diagram showing a circuit to incorporate a sensor output in spin current phase data.
Figure 14:
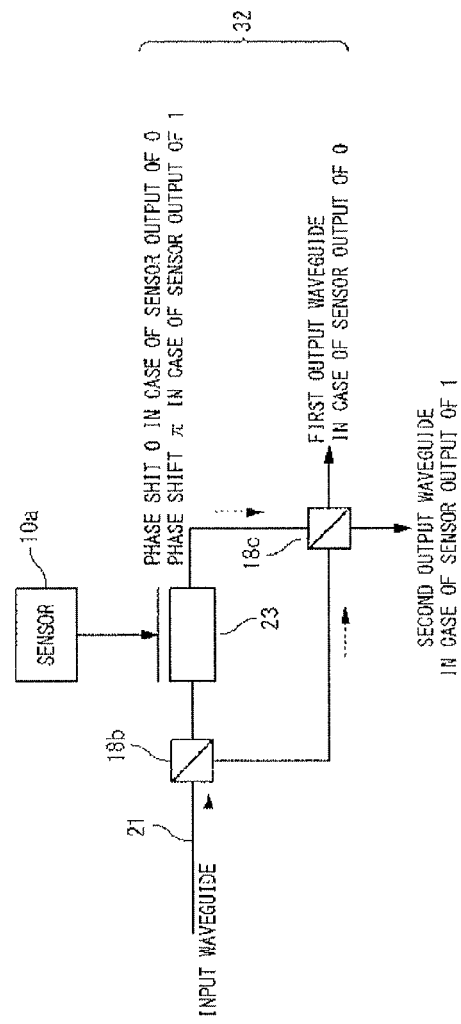
FIG. 14 is a graph showing another circuit to incorporate the sensor output into the spin current phase data.
Figure 15A:
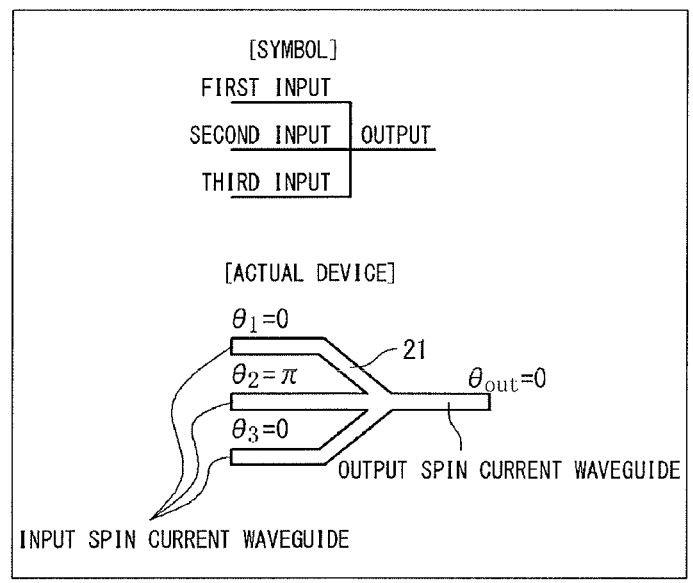
FIG. 15A is a diagram showing a majority gate circuit using a spin current.
Figure 15B:
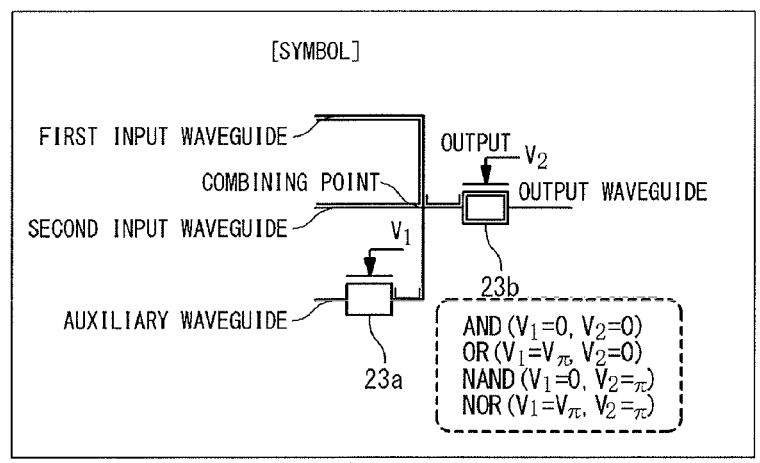
FIG. 15B is a block diagram showing a basic boolean algebra gate circuit using a spin current.
Figure 16:
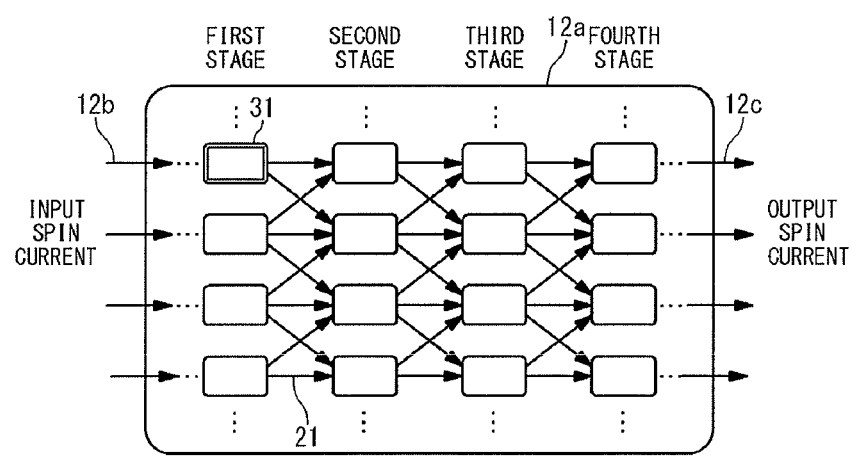
FIG. 16 is a block diagram schematically showing the configuration of a spin current processing circuit.
Figure 17:
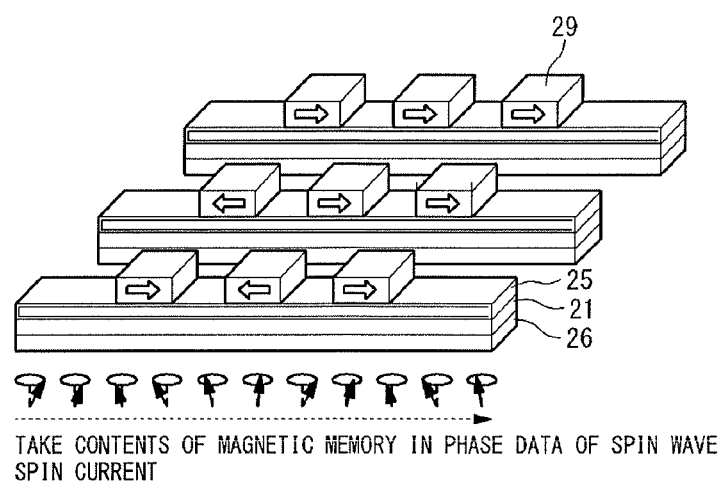
FIG. 17 is a diagram schematically showing a method of incorporating data stored in the magnetic memory into the spin current phase data.

FIG. 13 is a circuit diagram showing a circuit for incorporating a sensor output into spin current phase data. FIG. 14 is a block diagram showing another circuit by which the sensor output is incorporated in the spin current phase data. FIG. 15A is a diagram schematically showing a majority gate by the spin current. FIG. 15B is a block diagram schematically showing a basic boolean operation gate by the spin current. FIG. 16 is a block diagram schematically showing the configuration of a spin current processing circuit which is contained in the signal processing section 12. FIG. 17 is a diagram schematically showing a method of incorporating data stored in the magnetic memory into the spin current phase data.

The signal processing section 12 first incorporates the sensing data from various sensors 10a into the spin current generated by the spin current generating section 11 and carries out the signal processing (FIG. 3). In the circuit shown in FIG. 13, the sensing data (the sensor output) is incorporated into the spin wave spin current by the spin current modulator 23. Specifically, the sensor output is supplied to the spin current modulator 23 as the control signal. The spin current modulator 23 shifts the phase of the spin wave spin current by $\Delta\theta$ in response to the control signal (sensor output). Thus, the sensing data (the sensor data) is reflected on the phase of the spin wave spin current.

Also, when the sensor output shows "0" or "1", the output destination of the spin current can be changed based on the sensor output, by using the spin current interference device 32 shown in FIG. 14. Therefore, the sensor output can be reflected on the data (route data) indicating a route to which the spin current is outputted. The spin current interference device 32 has two spin current partial reflection mirrors 18b and 18c (reflectivity r=50%) and the spin current modulator 23. An inputted spin wave spin current is divided into two by the 3-terminal type spin current partial reflection mirror 18b. The phase of one of the spin wave spin currents is shifted by the spin current modulator 23 according to the sensor output. In the 4-terminal type spin current partial reflection mirror 18c, the spin wave spin current with the phase shifted and the other spin wave spin current interfere with each other. As a result, the propagation route of the spin wave spin current can be changed based on the sensor output. For example, it is supposed that the phase shift amount of the spin current in the spin current modulator 23 is "0" when the sensor output is "0", and the phase shift amount is "$\pi$" when the sensor output is "1". In this case, by the interference in the 4-terminal type spin current partial reflection mirror 18c, the spin wave spin current is outputted to the first output waveguide when the sensor output is "0", and the spin wave spin current is outputted to the second output waveguide when the sensor output is "1". Thus, the route on which the spin wave spin current propagates can be changed according to the sensor data. That is, the sensor data can be incorporated into the data (the route data) showing the route on which the spin wave spin current propagates.

The signal processing is carried out by using the data (the phase data) showing the phase of the spin wave spin current or the route data after incorporating the sensing data. For example, if the phase of the spin wave spin current is used as a state variable, various basic calculation gates (processing circuits) shown below can be configured.

FIG. 15A is a diagram showing an example of a majority gate circuit and a symbol. The majority gate circuit shown in FIG. 15A has the spin current waveguides for three inputs and the spin current waveguide for output. The spin waveguides for three inputs are connected with the spin current waveguide for output. The three spin wave spin currents are led from the spin current waveguides for three inputs to the spin current waveguide for output. In the spin current waveguide for output, the three spin wave spin currents interfere with each other. Thus, the majority gate having three inputs and one output can be configured. It is supposed that the state variable is "0" when the phase of the spin wave spin current is "0", and the state variable is "1" when the phase is "$\pi$". The major state variables or (equal to or more than two) state variables on the three spin current waveguides 21 appears on the waveguide for output.

Moreover, by combining this majority gate and the spin current modulators 23 shown in FIG. 12B to FIG. 12G, a basic boolean operation gate (AND circuit, OR circuit and so on) having two inputs and one output can be configured.

FIG. 15B is a diagram showing an example of such a basic boolean operation gate. The basic boolean operation gate shown in FIG. 15B has a waveguide for a first input, a waveguide for a second input, an auxiliary waveguide, spin current modulators 23a and 23b and an output waveguide. The first input waveguide, the second input waveguide and the auxiliary waveguide are combined at a combination point and are connected with the output waveguide. The spin current modulator 23a is provided for the auxiliary waveguide. The spin current modulator 23b is provided for the output waveguide. A control signal V1 is supplied to the spin current modulator 23a. A control signal V2 is supplied to the spin current modulator 23b. Also, in the same way, by combining the spin current interference device 32 (FIG. 14) and the spin current modulator 23 (FIG. 12A to FIG. 12G), a basic calculation gate (AND circuit, OR circuit and so on) can be configured which uses the route data generated by the spin current interference device 32 as a state variable.

When the spin current waveguide 21 is configured from the insulator such as YIG, the spin wave spin current maintains coherence (easiness of interference) over a comparatively long distance. FIG. 16 is a diagram showing an example of the spin current processing circuit 12a. The spin current processing circuit has a plurality of stages and a plurality of basic calculation gates 31 are provided for each stage. The outputs of the basic calculation gate 31 provided for each stage are connected with the inputs of the plurality of basic calculation gates 31 provided for the latter stage. The inputs of the plurality of basic calculation gates 31 provided for the first stage configure an input section 12b. The inputted spin current is inputted to the spin current processing circuit 12a through the input section 12b. The outputs of the basic calculation gates 31 provided for the last stage configures an output section 12c. The output spin current is outputted from the spin current processing circuits 12b to the output section 12c. In the spin current processing circuit 12a shown in FIG. 16, when the input spin currents showing raw data from the sensors are supplied to the input section 12b, the processed data are taken out from the output section 12c. Because the spin current in the insulator is not accompanied by the generation of the joule heat, the energy dissipation from the input section 12b to the output section 12c is very small. As a result, the energy efficiency in the spin current processing circuit 12a can be improved.

It should be noted that if the spin current modulator 23 is used which is reconfigurable as shown in FIG. 12E and FIG. 12F, the reconfigurable calculation gate can be configured. Because the magnetic terminal 29 and the domain wall 21d have a nonvolatile property, the processing circuit can be configured in which a signal processing procedure is stored in a non-volatile manner. For example, thus, the standing-by power can be reduced by using a sleep mode and so on.

Also, a circuit for reflecting data (sensor ID and so on) stored in the magnetic memory on the spin wave spin current by using the modulation technique due to the magnetic terminal 29 and the domain wall 21d. FIG. 17 is a diagram schematically showing a circuit for reflecting the data stored in the magnetic memory on the spin wave spin current. The plurality of magnetic terminals 29 are formed through the barrier film 25 on the spin current waveguides 21. The degree of freedom of the directions of the magnetization in the plurality of magnetic terminals 29 shows the data stored in the magnetic memory. Through the magnetic interaction between the plurality of magnetic terminals 29 and the spin wave spin current, the data of the magnetic memory (FIG. 3) can be copied into the phase data of the spin wave spin current.

Next, the radio section 13 (FIG. 3) will be described with reference to the drawings.

In the signal processing section 12 (FIG. 3), processing such as the integration, arrangement and encryption of data is carried out. The spin wave spin current showing the sensing data is sent from the signal processing section 12 to the radio section 13. The phase data which the spin wave spin current has or the route data is copied into microwave generated in the radio section 13 and is transmitted to a base station and another terminal. As the radio section 13, it is possible to use the microwave oscillator known conventionally, and the microwave oscillator using the resonance of the spin wave spin current and so on.

Figure 18:
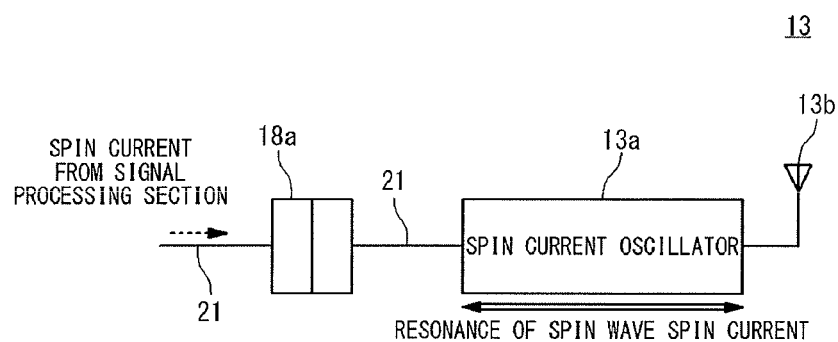
FIG. 18 is a diagram schematically showing the configuration of a radio section.

Among them, the radio section 13 using the resonance of the spin wave spin current is shown in FIG. 18. The radio section 13 has the 2-terminal type spin current partial reflection mirror 18a, the spin current oscillator 13a, and an antenna 13b. The input of the 2-terminal type spin current partial reflection mirror 18a is connected with the output of the signal processing section 12 through the spin current waveguide 21. The output of the 2-terminal type spin current partial reflection mirror 18a is connected with the input of the spin current oscillator 13a through the spin current waveguide 21. The output of the spin current oscillator 13a is connected with the antenna 13b through the spin current waveguide 21. The spin wave spin current outputted from the signal processing section 12b is supplied to the spin current oscillator 13a through the 2-terminal type spin current partial reflection mirror 18a. When the spin wave spin current is supplied to the spin current oscillator 13a, the microwave oscillation happens.

Figure 19:
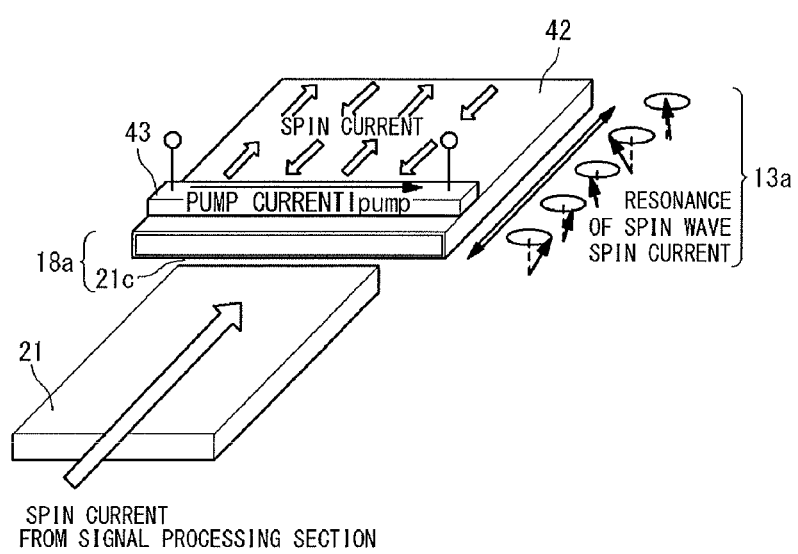
FIG. 19 is a diagram schematically showing the configuration of a spin current oscillator.

A microwave oscillation mechanism of the spin current oscillator 13a will be described. FIG. 19 is a diagram schematically showing the configuration of the spin current oscillator 13a. As shown in FIG. 19, the spin current oscillator 13a has a magnetic insulator resonator 42 and a pump metal terminal 43 arranged on the magnetic insulator resonator 42. The pump metal terminal 43 is configured for pump electric current Ipump to flow therethrough. The spin wave spin current outputted from the signal processing section 12 is supplied to the magnetic insulator resonator 42 through the 2-terminal type spin current partial reflection mirror 18a. The supplied spin wave spin current is amplified by the pump electric current Ipump which flows through the pump metal terminal 43. Moreover, the amplified spin wave spin current is reflected in a multiple manner at the end face of the magnetic insulator resonator 42. At this time, when the pump electric current Ipump exceeds a threshold value electric current, the spin wave spin current resonates in the magnetic insulator resonator 42. As a result, the oscillation in the microwave frequency occurs.

It should be noted that the microwave oscillation in this case is generated based on the supplied spin wave spin current (as the species). Thus, the phase data which the spin wave spin current has or the route data can be copied into the microwave data. For example, when the data is superimposed on the phase of the spin wave spin current, the phase of supplied spin wave spin current is reflected on the phase of the microwave generated with the oscillation.

For example, as the magnetic insulator resonator 42, the YIG film and so on can be used. For example, this YIG film can be formed by using a liquid phase epitaxy (LPE) and a laser ablation method (Pulsed Laser Deposition (PLD)) and so on. Also, as the pump metal terminal 43, it is desirable to use the material that the spin Hall effect appears efficiently. Specifically, the pump metal terminal 43 can be obtained by sputtering Pt, Au, Pd, Ag, Bi or these alloys.

The microwave generated through the oscillation is transmitted to the base station and the other terminal by the antenna 13b. As the antenna 13b, a conventional antenna such as a dipole-type antenna can be used. In this way, the spin current showing the sensing data can be converted into the microwave just as it is and can be transmitted. The radio communication of high energy efficiency becomes possible.

According to the present exemplary embodiment, the spin current can be generated from various heat sources 20 (solar heat, body temperature, various types of waste heat and so on). The sensing data can be taken into the generated spin current. Also, the simple signal processing (integration, arrangement and encryption and so on) can be carried out. In addition, a microwave for the radio communication can be oscillated by using the spin current into which data is incorporated. Moreover, in the waveguide 21, the spin current in the magnetic insulator (e.g. YIG film 21b) is not accompanied by the generation of the joule heat. Therefore, the information transmission and information processing of the small energy dissipation become possible and the platform of high energy efficiency can be realized. Also, because the spin current is used in the spin current generating section 11 which drives the sensor section 10 and the signal processing section 12, the platform of the high energy efficiency is realized. Also, if a magnetic material (magnetic terminal 29, domain wall 21d and so on) is used as a gate terminal in the spin current modulator 23, the reconfigurable circuit can be configured which can store a procedure and so on in a non-volatile manner. Therefore, the standby power can be reduced by the use of the sleep mode and so on. Moreover, because the spin current into which the sensing data is incorporated is converted into the microwave just as it is, the radio communication of the high energy efficiency becomes possible.

This application claims a priority on convention based on Japanese Patent Application JP 2010-070610. The disclosure thereof is incorporated herein by reference.

The invention claimed is:

1. A thermal sensor comprising:
a detecting film configured to generate heat through incidence or adhesion of an object to be detected;
a magnetic film configured to generate a spin current in a direction of a temperature gradient by the heat generated by said detecting film; and
an electrode configured to convert the spin current generated by said magnetic film into an electric current,
wherein the detecting film, the magnetic film and the electrode are stacked in a first direction, and
wherein the direction of the temperature gradient by the heat generated by the detecting film is in said first direction.

2. The thermal sensor according to claim 1, wherein said detecting film is an infrared ray absorption film configured to generate the heat by absorbing at least a part of an infrared ray.

3. The thermal sensor according to claim 1, wherein said magnetic film comprises a magnetic insulator.

* * * * *